(12) United States Patent
Kamatani et al.

(10) Patent No.: US 9,145,344 B2
(45) Date of Patent: Sep. 29, 2015

(54) ORGANIC COMPOUND AND ORGANIC LIGHT-EMITTING DEVICE INCLUDING THE SAME

(75) Inventors: Jun Kamatani, Tokyo (JP); Naoki Yamada, Inagi (JP); Kengo Kishino, Tokyo (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 373 days.

(21) Appl. No.: 13/701,665

(22) PCT Filed: May 26, 2011

(86) PCT No.: PCT/JP2011/062644
§ 371 (c)(1),
(2), (4) Date: Dec. 3, 2012

(87) PCT Pub. No.: WO2011/152477
PCT Pub. Date: Dec. 8, 2011

(65) Prior Publication Data
US 2013/0076604 A1    Mar. 28, 2013

(30) Foreign Application Priority Data

Jun. 4, 2010  (JP) .................................. 2010-129267

(51) Int. Cl.
*C07C 13/62*   (2006.01)
*C07C 211/61*   (2006.01)
(Continued)

(52) U.S. Cl.
CPC ................ *C07C 13/62* (2013.01); *C07C 25/22* (2013.01); *C07C 43/285* (2013.01);
(Continued)

(58) Field of Classification Search
CPC .. C07C 13/62; C07C 2103/54; C07C 211/61; C07C 25/22; C07C 43/285; C07D 209/86; C07D 213/06; C07D 213/16; C07D 215/06; C07D 333/54; C07F 7/0809; C09K 11/06; C09K 2211/1011; C09K 2211/1029; C09K 2211/1037; G09G 3/3208; H01L 27/3225; H01L 51/0032; H01L 51/0056; H01L 51/0058; H01L 51/006; H01L 51/5012; H01L 51/50; H01L 51/54; H05B 33/14
See application file for complete search history.

(56) References Cited

U.S. PATENT DOCUMENTS

| | | | |
|---|---|---|---|
| 2002/0168544 A1* | 11/2002 | Fukuoka et al. | 428/690 |
| 2004/0076853 A1* | 4/2004 | Jarikov | 428/690 |
| 2014/0231787 A1* | 8/2014 | Ishige et al. | 257/40 |

FOREIGN PATENT DOCUMENTS

| | | |
|---|---|---|
| CN | 101541712 A | 9/2009 |
| JP | 2008-235734 A | 10/2008 |
| JP | 2008-300753 A | 12/2008 |

OTHER PUBLICATIONS

Chemistry—A—European Journal, Kung Yun-Hua et al., Apr. 15, 2010 vol. 16, p. 5909-5919.
(Continued)

*Primary Examiner* — Dawn Garrett
(74) *Attorney, Agent, or Firm* — Canon U.S.A. Inc., IP Division

(57) ABSTRACT

Provided are a novel organic compound appropriate for emission of green light and an organic light-emitting device including the organic compound. Provided is a substituted or unsubstituted indeno[1,2,3-cd]naphtho[2,3-k]fluoranthene appropriate for emission of green light. The substituents of the indeno[1,2,3-cd]naphtho[2,3-k]fluoranthene are each independently selected from a hydrogen atom, a halogen atom, a substituted or unsubstituted alkyl group, a substituted or unsubstituted alkoxy group, a substituted amino group, a substituted or unsubstituted aryl group, and a substituted or unsubstituted heterocyclic group.

12 Claims, 1 Drawing Sheet

(51) Int. Cl.
| | |
|---|---|
| C07C 25/22 | (2006.01) |
| C07C 43/285 | (2006.01) |
| C07D 209/86 | (2006.01) |
| C07D 213/06 | (2006.01) |
| C07D 213/16 | (2006.01) |
| C07D 215/06 | (2006.01) |
| C07D 333/54 | (2006.01) |
| C07F 7/08 | (2006.01) |
| G09G 3/32 | (2006.01) |
| H01L 51/00 | (2006.01) |
| C09K 11/06 | (2006.01) |
| H05B 33/14 | (2006.01) |
| H01L 27/32 | (2006.01) |
| H01L 51/50 | (2006.01) |

(52) U.S. Cl.
CPC ........... *C07C 211/61* (2013.01); *C07D 209/86* (2013.01); *C07D 213/06* (2013.01); *C07D 213/16* (2013.01); *C07D 215/06* (2013.01); *C07D 333/54* (2013.01); *C07F 7/0809* (2013.01); *C09K 11/06* (2013.01); *G09G 3/3208* (2013.01); *H01L 27/3225* (2013.01); *H01L 51/0032* (2013.01); *H01L 51/0056* (2013.01); *H05B 33/14* (2013.01); *C07C 2103/54* (2013.01); *C09K 2211/1011* (2013.01); *C09K 2211/1029* (2013.01); *C09K 2211/1037* (2013.01); *H01L 51/006* (2013.01); *H01L 51/0058* (2013.01); *H01L 51/5012* (2013.01)

(56) References Cited

OTHER PUBLICATIONS

E J. W. List et al., Excitation energy migration assisted processes in conjugated polymers, Synthetic Metals, vol. 141, Issues 1-2, Mar. 18, 2004, p. 211-218.

E J. W. List et al., Excitation energy migration in highly emissive semiconducting polymers, Chemical Physics Letters, Jul. 21, 2000, vol. 325, p. 132-138.

Yun Hua Kung, Yu-Sung Cheng, Chia-Cheng Tai, Wei-Szu Liu; Synthesis, Structures and Physical Properties . . . Acenes; Apr. 15, 2010.

* cited by examiner

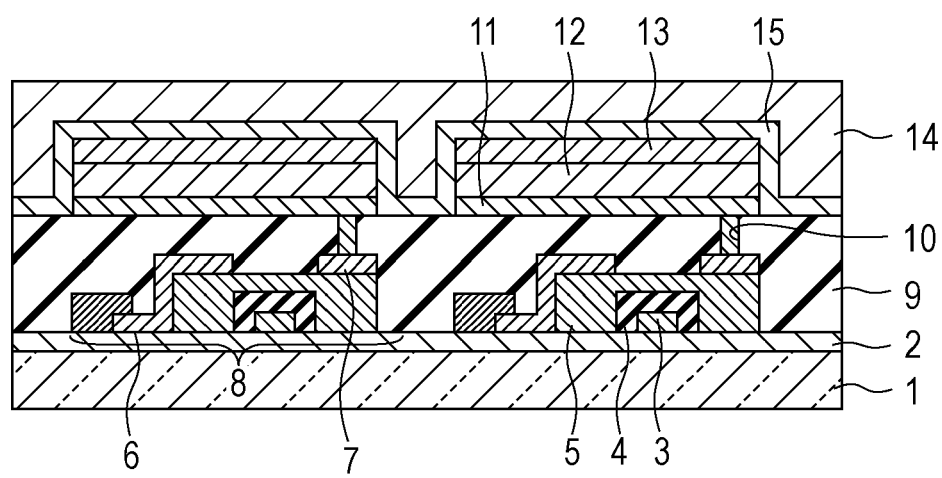

ORGANIC COMPOUND AND ORGANIC LIGHT-EMITTING DEVICE INCLUDING THE SAME

TECHNICAL FIELD

The present invention relates to novel organic compounds and organic light-emitting devices including such organic compounds.

BACKGROUND ART

An organic light-emitting device includes an anode, a cathode, and an organic compound layer disposed therebetween. When the two electrodes inject electrons and holes into the organic compound layer, an organic compound contained therein generates excitons and emits light as the excitons return to the ground state.

Organic light-emitting devices are also referred to as organic electroluminescent (EL) devices.

The development of novel luminescent organic compounds has so far been intensively conducted. The development of such compounds is important to provide high-performance organic light-emitting devices.

As an example of such an organic compound, PTL 1 discloses exemplary compound 1-A:

[Chem. 1]

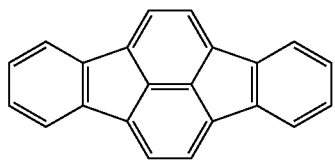

(1-A)

As another example of such an organic compound, PTL 2 discloses exemplary compound 1:

[Chem. 2]

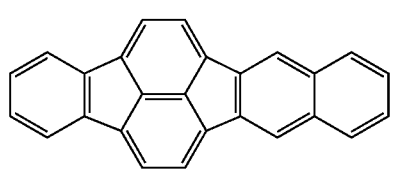

(Exemplary compound 1)

CITATION LIST

Patent Literature

PTL 1 Japanese Patent Laid-Open No. 2008-235734 (no foreign counterpart)
PTL 2 Japanese Patent Laid-Open No. 2008-300753 (no foreign counterpart)

SUMMARY OF INVENTION

The organic compounds disclosed in PTL 1 and 2 hardly emit light by themselves. Both of exemplary compounds 1-A and 1, as shown in the above formulas, are composed of unsubstituted fused rings. In other words, these organic compounds have basic backbones represented by the above structural formulas.

Accordingly, the present invention provides a novel organic compound that can emit light only with the basic backbone thereof and that can light in the green region.

According to an aspect of the present invention, there is provided an organic compound represented by general formula (1):

[Chem. 3]

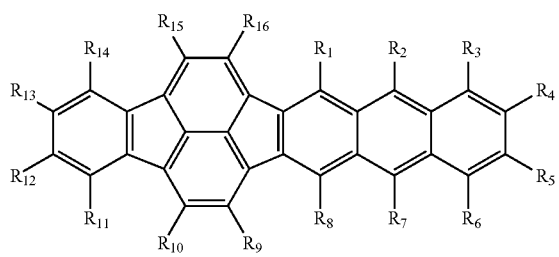

(1)

In formula (1), $R_1$ to $R_{16}$ are each independently selected from a hydrogen atom, a halogen atom, a substituted or unsubstituted alkyl group, a substituted or unsubstituted alkoxy group, a substituted amino group, a substituted or unsubstituted aryl group, and a substituted or unsubstituted heterocyclic group.

According to the above aspect of the present invention, a novel organic compound having a wide bandgap and a deep LUMO level only with the basic backbone thereof can be provided. Thus, the organic compound emits light in the green region only with the backbone thereof. In addition, introducing a substituent to the backbone provides a novel organic compound capable of emitting red light, rather than green light. Furthermore, an organic light-emitting device including such a novel organic compound can be provided.

BRIEF DESCRIPTION OF DRAWING

FIG. 1 is a schematic sectional view of organic light-emitting devices and switching devices connected to the organic light-emitting devices.

DESCRIPTION OF EMBODIMENTS

An organic compound according to an embodiment of the present invention is represented by general formula (1):

[Chem. 4]

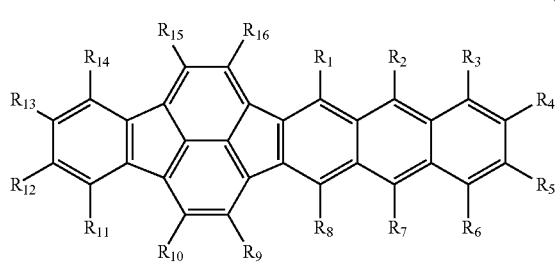

(1)

In formula (1), $R_1$ to $R_{16}$ are each independently selected from a hydrogen atom, a halogen atom, a substituted or unsubstituted alkyl group, a substituted or unsubstituted alkoxy group, a substituted amino group, a substituted or unsubstituted aryl group, and a substituted or unsubstituted heterocyclic group.

The aryl group and the heterocyclic group can be substituted with an alkyl group.

The amino group can be substituted with an alkyl or aryl group.

In formula (1), the alkyl group can be, for example, methyl, ethyl, n-propyl, isopropyl, n-butyl, isobutyl, sec-butyl, tert-butyl, octyl, 1-adamantyl, or 2-adamantyl.

In formula (1), the alkoxy group can be, for example, methoxy, ethoxy, propoxy, 2-ethyloctyloxy, phenoxy, 4-tert-butylphenoxy, benzyloxy, or thienyloxy.

In formula (1), the amino group can be, for example, N-methylamino, N-ethylamino, N,N-dimethylamino, N,N-diethylamino, N-methyl-N-ethylamino, N-benzylamino, N-methyl-N-benzylamino, N,N-dibenzylamino, anilino, N,N-diphenylamino, N,N-dinaphthylamino, N,N-difluorenylamino, N-phenyl-N-tolylamino, N,N-ditolylamino, N-methyl-N-phenylamino, N,N-dianisolylamino, N-methyl-N-phenylamino, N,N-dimesitylamino, N-phenyl-N-(4-tert-butylphenyl)amino, or N-phenyl-N-(4-trifluoromethylphenyl)amino.

In formula (1), the aryl group can be, for example, phenyl, naphthyl, indenyl, biphenyl, terphenyl, or fluorenyl.

In formula (1), the heterocyclic group can be, for example, pyridyl, oxazolyl, oxadiazolyl, thiazolyl, thiadiazolyl, carbazolyl, acridinyl, or phenanthrolyl.

The present inventors have focused attention on molecules, composed only of a basic backbone, that have peak emission wavelengths falling within the intended emission wavelength region. The basic backbone according to this embodiment is represented by the following structural formula:

[Chem. 5]

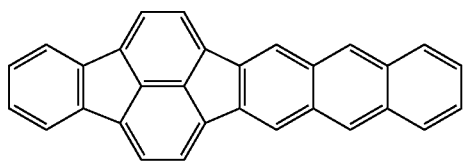

Although it is known that the basic backbone of a compound can be substituted to achieve the intended emission wavelength, it may impair the stability of the compound. It is therefore important in view of the stability of a compound that the molecule be composed only of a basic backbone and have a peak emission wavelength as close to the intended emission wavelength as possible.

In this embodiment, the intended emission wavelength region is the green region, specifically, 480 to 530 nm in peak emission wavelength.

Comparison between Basic Backbone of Organic Compound According to Embodiment and Other Basic Backbones The basic backbone of the organic compound according to this embodiment will now be compared with the following basic backbones:

[Chem. 6]

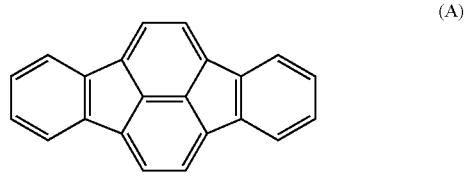

(A)

[Chem. 7]

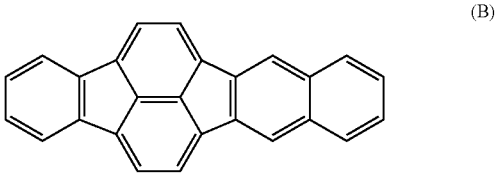

(B)

An organic compound (c in Table 1) prepared by substituting the basic backbone of the organic compound according to this embodiment with phenyl groups, an organic compound (a in Table 1) that is an unsubstituted basic backbone represented by formula (A), and an organic compound (b in Table 1) prepared by substituting the basic backbone represented by formula (B) with phenyl groups were compared for emission characteristics. The symbol "-" in the table means that no emission is observed in the ultraviolet and visible regions.

TABLE 1

| | Structural formula | Peak emission wavelength (nm) | Quantum yield |
|---|---|---|---|
| a | | — | <0.01 |

TABLE 1-continued

| Structural formula | Peak emission wavelength (nm) | Quantum yield |
|---|---|---|
| b 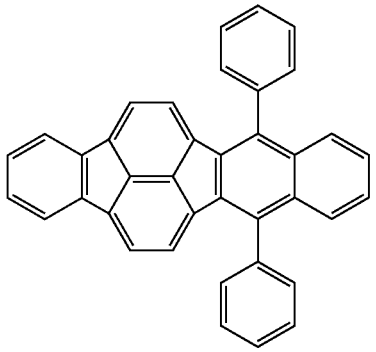 [SMILES: c1ccc(-c2c3c(c(-c4ccccc4)c4ccccc24)-c2ccc4c5c(ccc-3c25)-c2ccccc2-4)cc1] | 550 | 0.05 |
| c 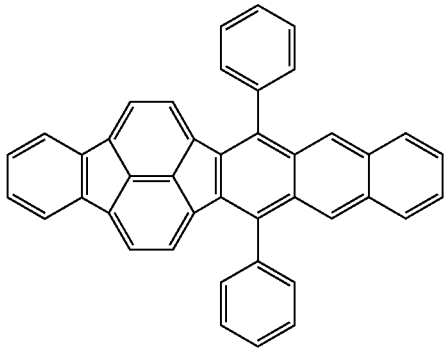 [SMILES: c1ccc(-c2c3c(c(-c4ccccc4)c4cc5ccccc5cc24)-c2ccc4c5c(ccc-3c25)-c2ccccc2-4)cc1] | 516 | 0.82 |

The organic compound shown as a in Table 1 hardly emits light in the ultraviolet and visible regions. Hence, the quantum yield cannot be measured. The organic compound shown as b in Table 1 slightly emits light. However, this compound emits yellow light with a peak emission wavelength of 550 nm because the luminous intensity is low at the vibrational level for 0-0 and is maximized at another vibrational level. That is, this compound has low luminous intensity and does not emit green light. The organic compound shown as c in Table 1 according to this embodiment has high quantum yield and emits green light with a peak emission wavelength of 516 nm.

Thus, the indeno[1,2,3-cd]fluoranthene backbone itself, shown as a in Table 1, is not suitable as a light-emitting material. Similarly, the organic compound shown as b in Table 1, which has a basic backbone formed by fusing a benzene ring to the above backbone, is not suitable as a light-emitting material because it emits yellow light and hardly emits light. In contrast, the organic compound shown as c in Table 1 according to this embodiment, which has a basic backbone formed by fusing a naphthalene ring to the indeno[1,2,3-cd]fluoranthene backbone in a direction in which the conjugation thereof is extended, emits green light and has high quantum yield.

Although increasing the number of fused rings for extended conjugation is generally assumed to change the color from blue to green, yellow, and red, the relationship between the structure shown as b in Table 1 and the structure shown as c in Table 1 according to this embodiment disagrees with the above assumption. That is, the compound shown as c in Table 1 is expected to emit red light from the color of light emitted from the compound shown as b in Table 1; against the expectation, the inventors have found that the compound shown as c in Table 1 emits green light.

In addition, the quantum yield of the organic compound shown as c in Table 1 according to this embodiment is at least ten times higher than that of the compound shown as b in Table 1.

[Chem. 8]

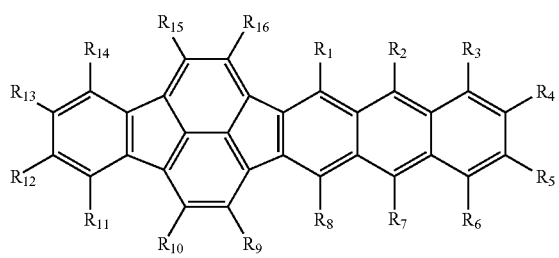

(1)

In addition, the basic backbone of the organic compound according to this embodiment is so flat that molecular stacking is likely to occur when a film is formed. This results in an emission wavelength longer than that of the molecule itself. To utilize the emission wavelength of the molecule alone when a film is formed, the present inventors believe that it is important to introduce a substituent to the basic backbone. The plane of the basic backbone of the organic compound according to this embodiment can make a nearly right dihedral angle with the plane of the substituent introduced thereto. In particular, it is effective to introduce an aryl group to at least one of $R_1$, $R_2$, $R_7$, and $R_8$.

In addition, the organic compound according to this embodiment has a deep HOMO energy level because it has two five-membered rings in the basic backbone thereof. That is, the organic compound according to this embodiment has low oxidation potential. Accordingly, the organic compound according to this embodiment is stable to oxidation.

In addition, the organic compound according to this embodiment does not have a heteroatom such as a nitrogen atom in the basic backbone thereof. This also contributes to the low oxidation potential, that is, the stability of the organic compound to oxidation.

The basic backbone of the organic compound according to this embodiment has a deep HOMO energy level. In view of the relationship between the HOMO and LUMO energy levels and the energy gap, this also means that the LUMO energy level is deep. Accordingly, the organic compound according to this embodiment easily accepts electrons.

The organic compound according to this embodiment serves not only as a green light-emitting material, but also as a red light-emitting material if the basic backbone has a substituent that makes the emission wavelength longer. This material with a longer wavelength is stable to oxidation because it has the same basic backbone as the organic compound according to this embodiment.

Examples of substituents for making the emission wavelength longer include triarylamine and anthracene. To adjust the emission wavelength, such a substituent can be introduced to at least one of $R_4$, $R_5$, $R_{12}$, and $R_{13}$ of the basic backbone of the organic compound according to this embodiment.

The organic compound according to this embodiment can be used as a guest or host material for a light-emitting layer of an organic light-emitting device. Specifically, the organic compound can be used as a guest material for a light-emitting layer, more specifically, a guest material for a light-emitting layer of a green light-emitting device.

If the organic compound according to this embodiment is used as a guest material for a light-emitting layer, the host material used can be an organic compound having a shallower LUMO level than the guest material, in other words, an organic compound whose LUMO level is closer to the vacuum level. This allows the guest material to more easily accept electrons supplied to the host material.

The term "host material" as used herein refers to a material having the highest weight fraction of the constituents of a light-emitting layer. The term "guest material" as used herein refers to a material having a lower weight fraction than the host material among the constituents of a light-emitting layer and responsible for emitting light. In addition, the term "assist material" as used herein refers to a material having a lower weight fraction than the host material among the constituents of a light-emitting layer and assisting the guest material in emitting light.

The organic compound according to this embodiment can also be used as a host material for a red light-emitting layer.

In addition, the organic compound according to this embodiment can be used as any of the layers other than a light-emitting layer, including a hole injection layer, a hole transport layer, a hole/exciton blocking layer, an electron transport layer, and an electron injection layer.

Examples of Organic Compounds According to Embodiment

Examples of organic compounds according to this embodiment include, but not limited to, the following compounds:

[Chem. 9]

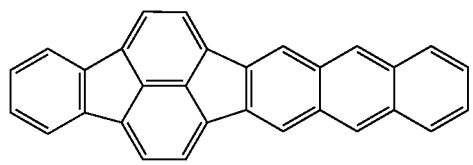

A1

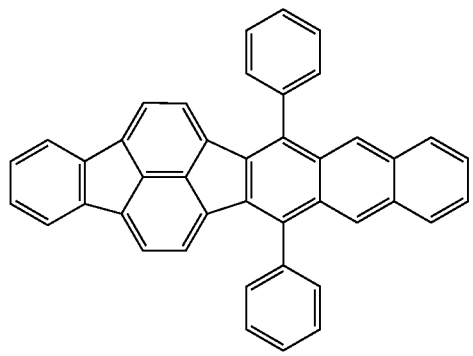

A2

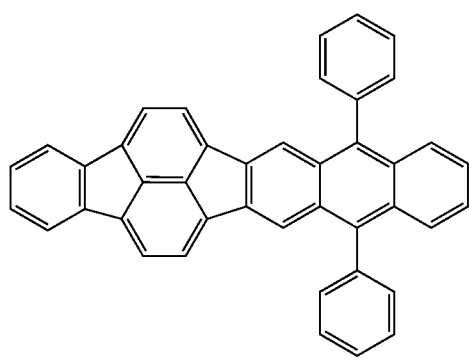

A3

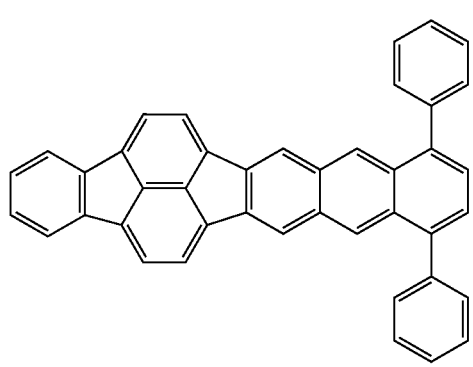

A4

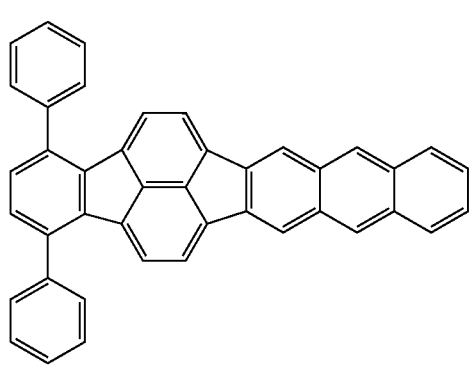

A5

A6
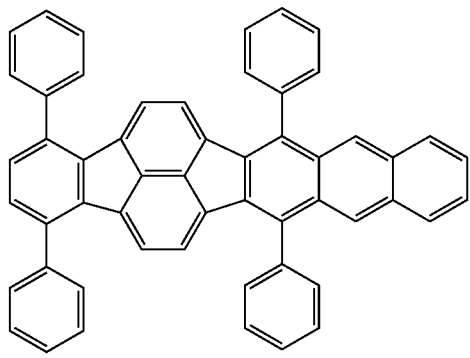
A7
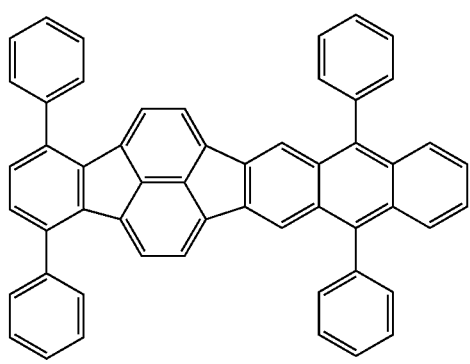
A8
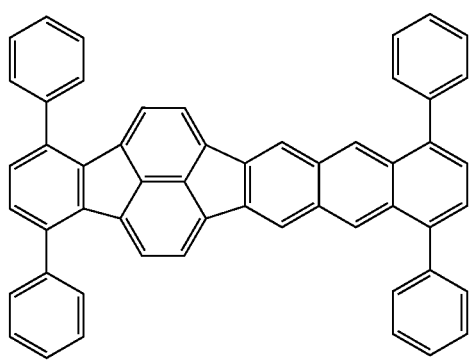
A9
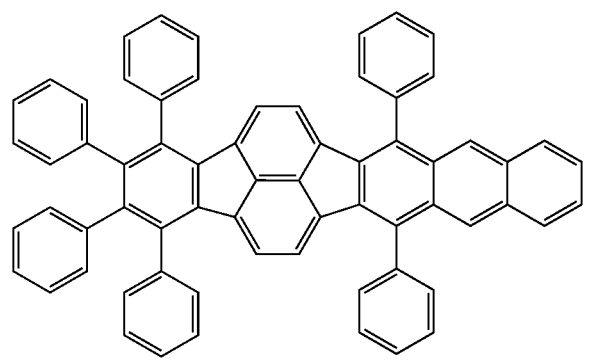
A10
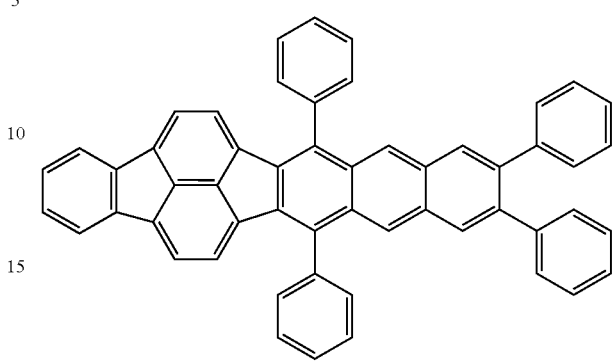
A11
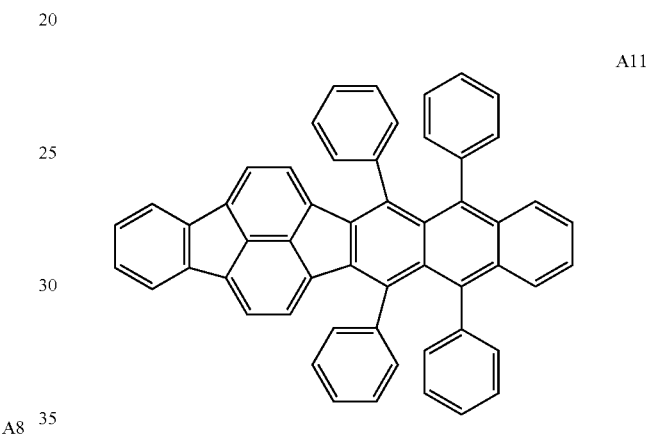
A12
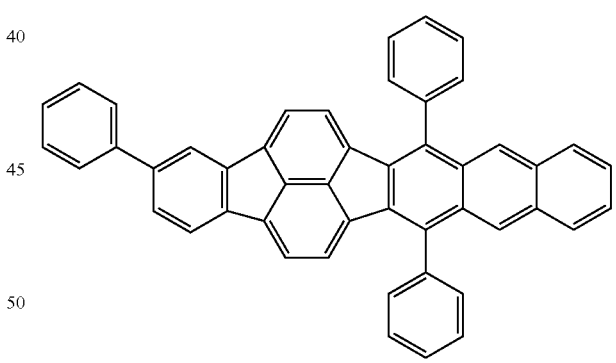
A13
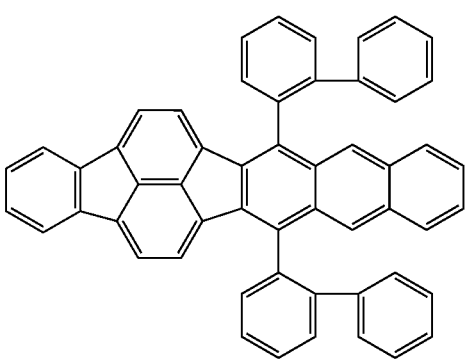

A14
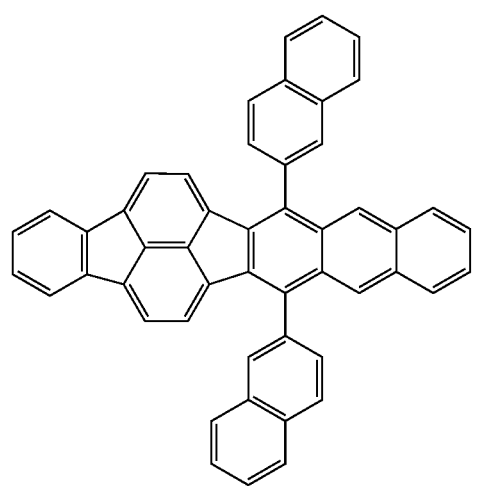
A15
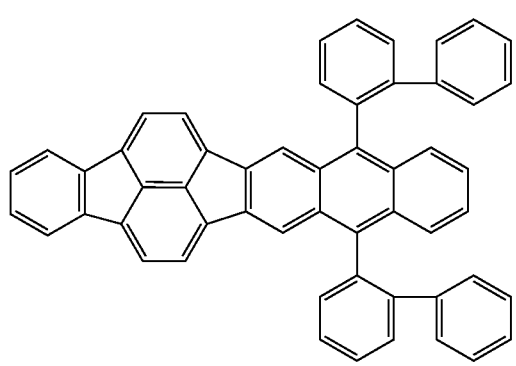
A16
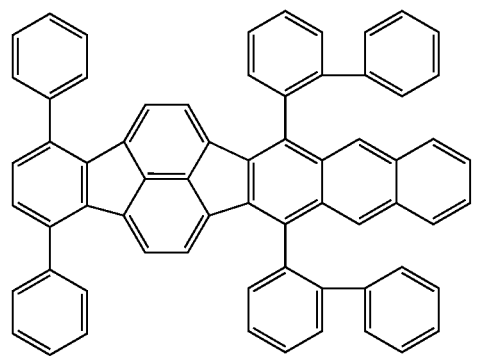
A17
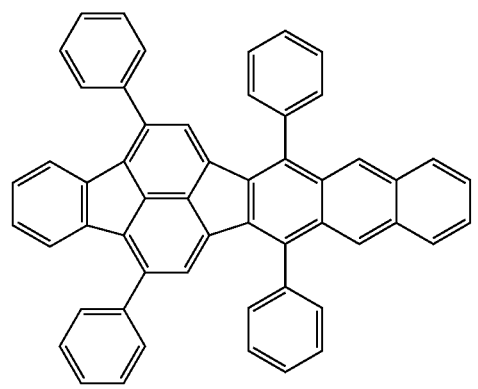
A18
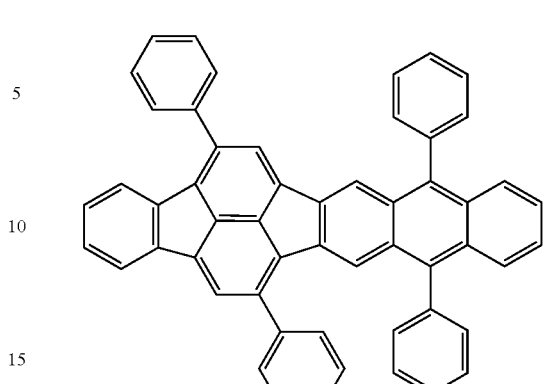
A19
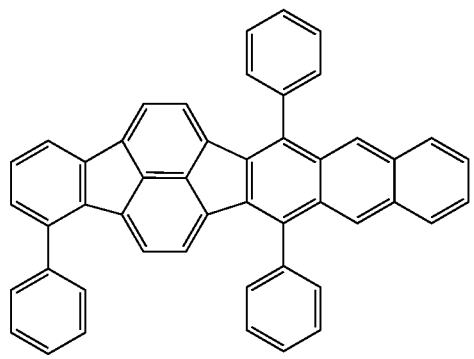
A20
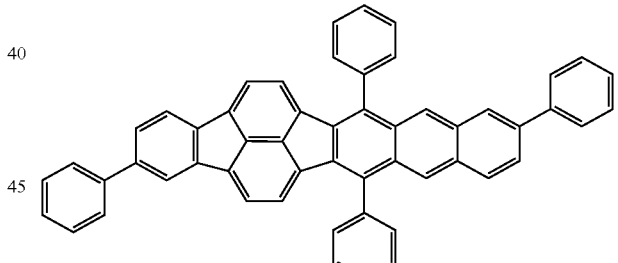
A21
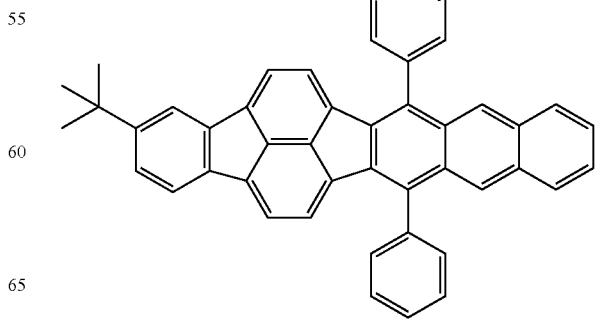

A22
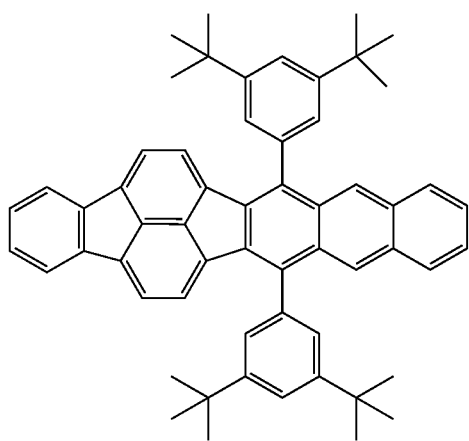
A23
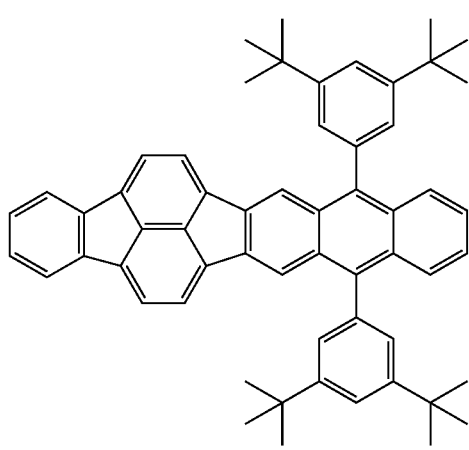
A24
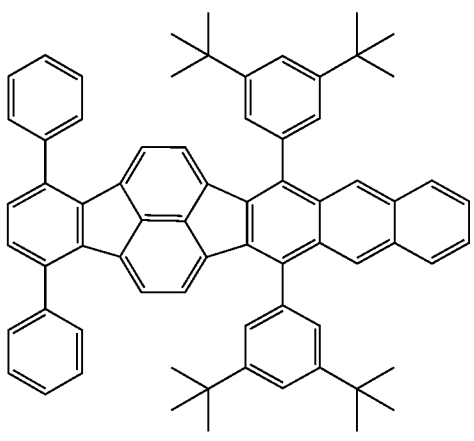
[Chem. 10]
A25
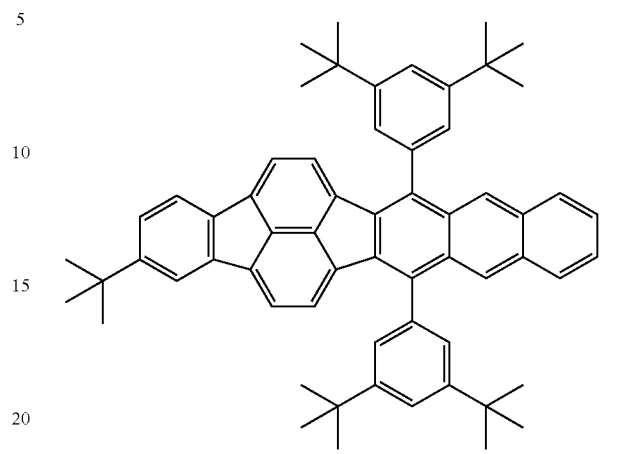
A26
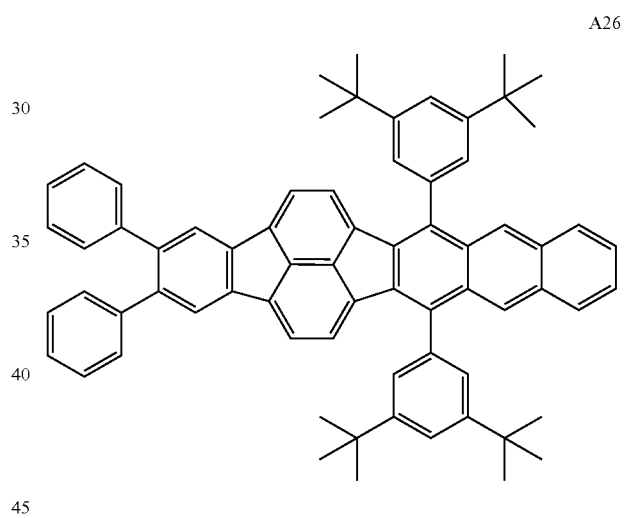
A27
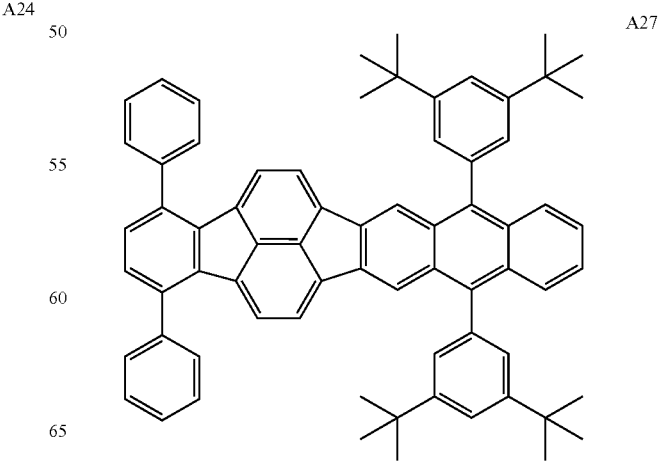

A28
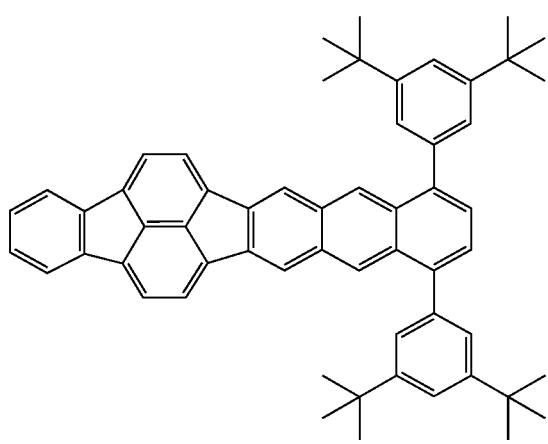
A31
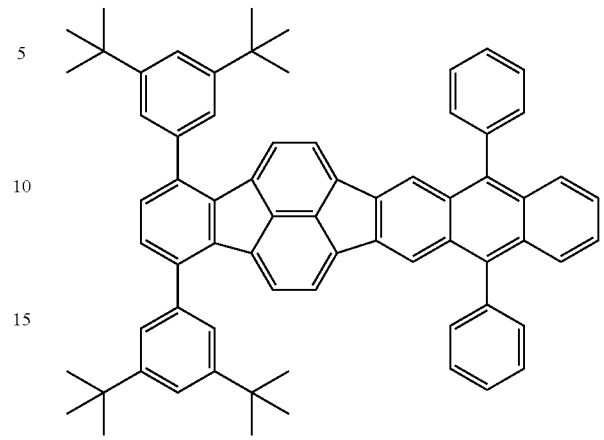
A29
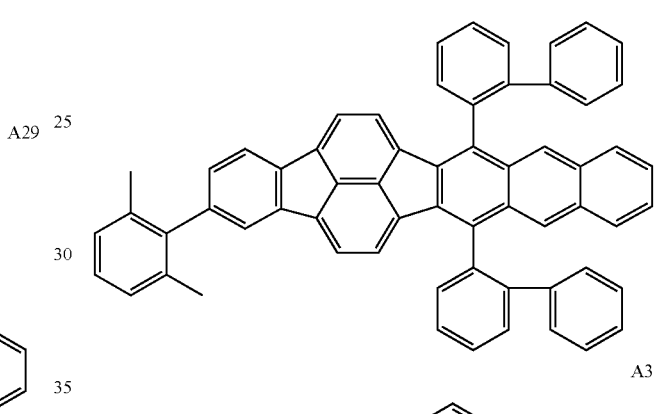
A32
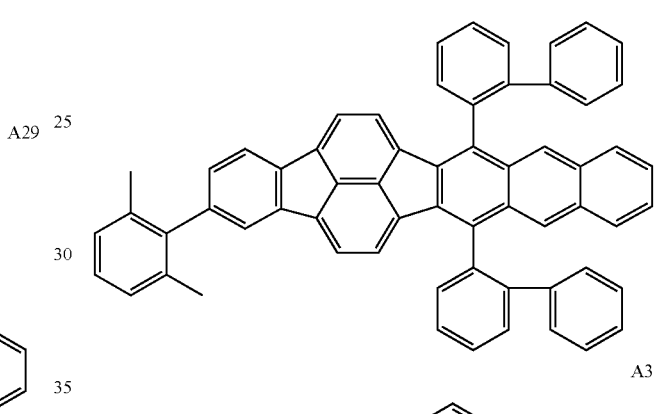
A30
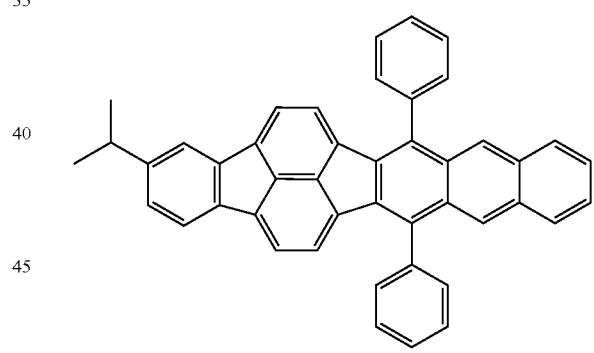
A33
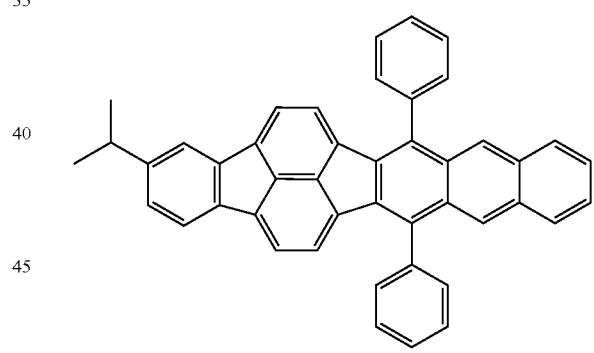
A34
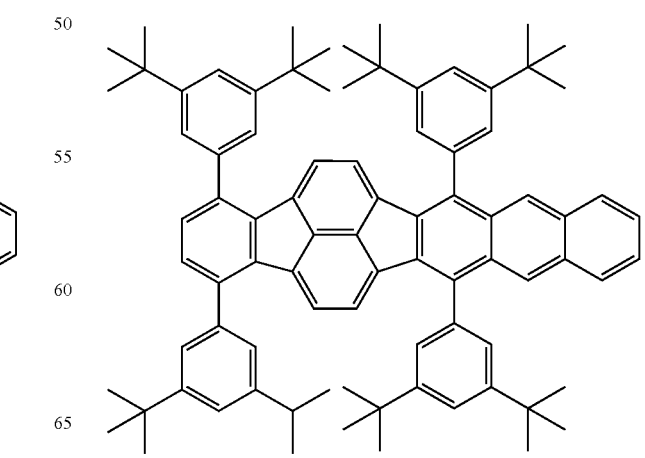

A35
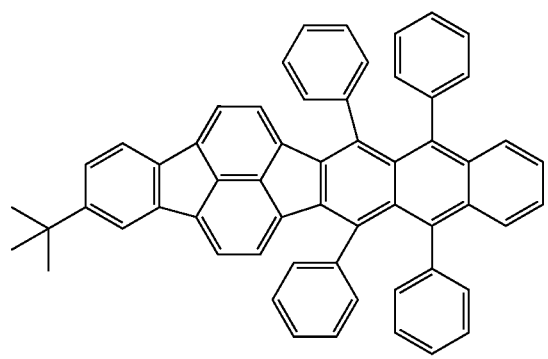
A38
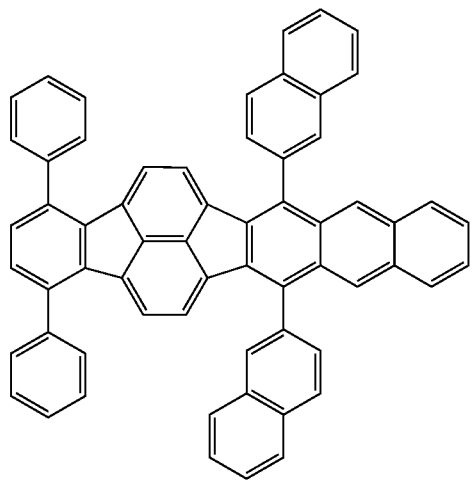
A36
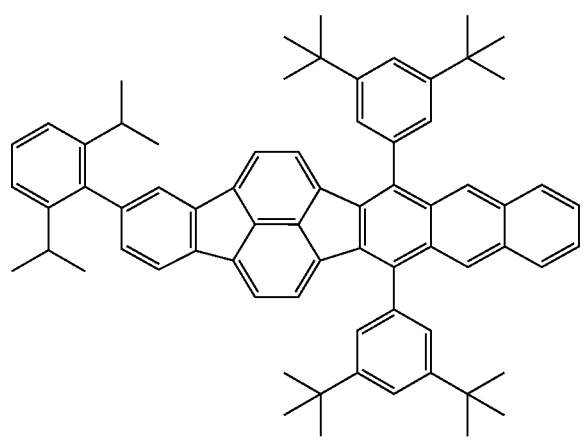
A39
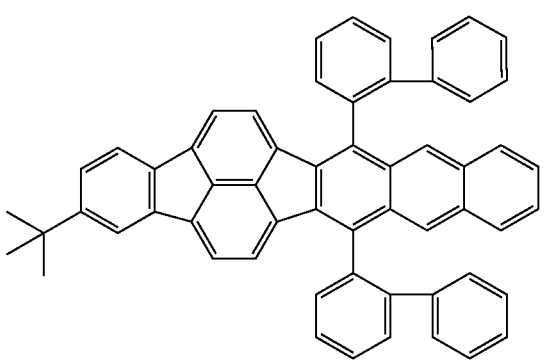
A37
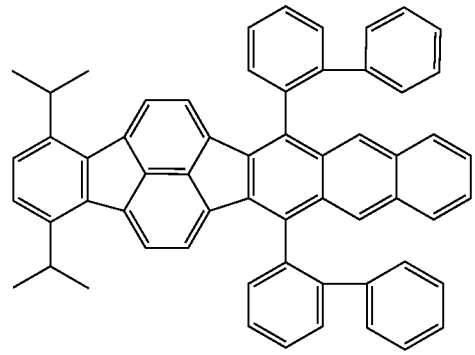
A40
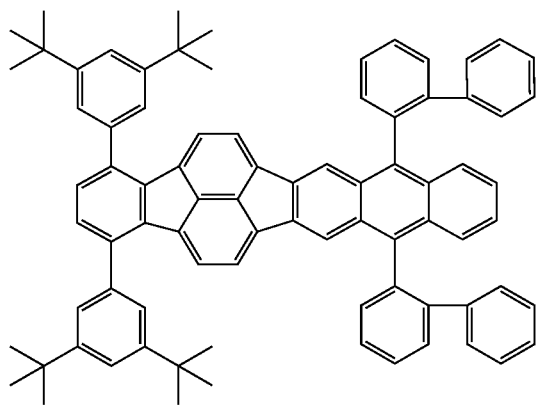

-continued
A41
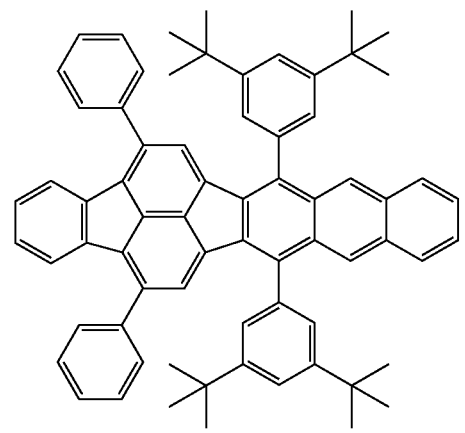
A42
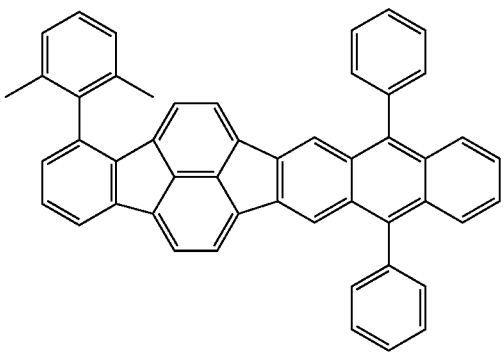
A43
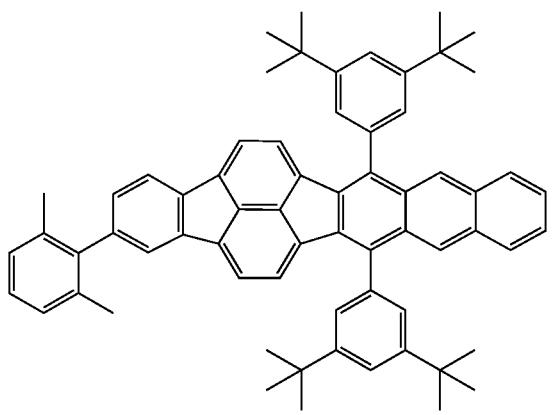
A44
-continued
A45
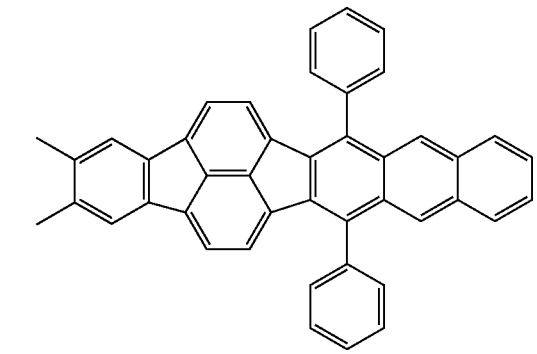
A46
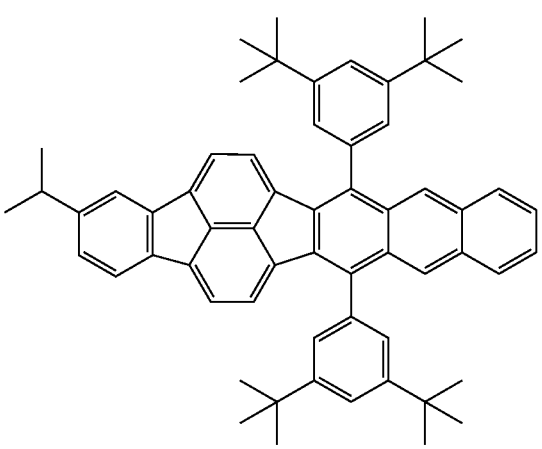
A47
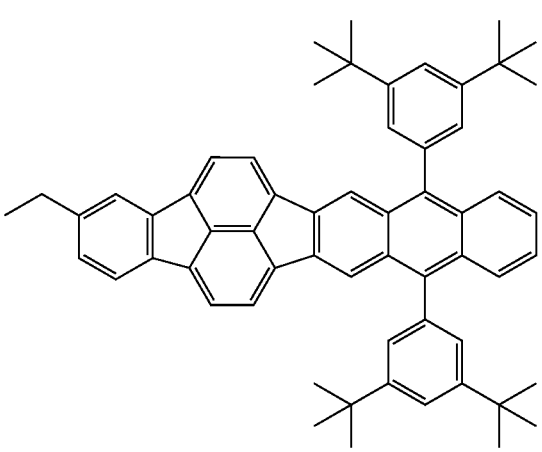

A48
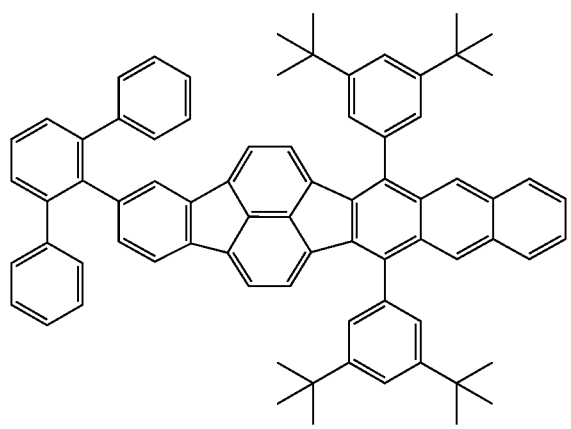
[Chem. 11]
B1
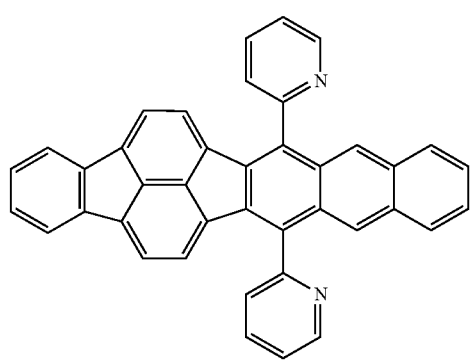
B2
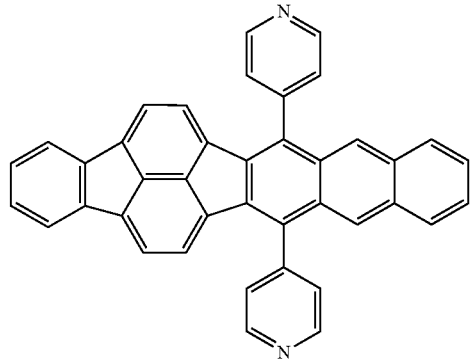
B3
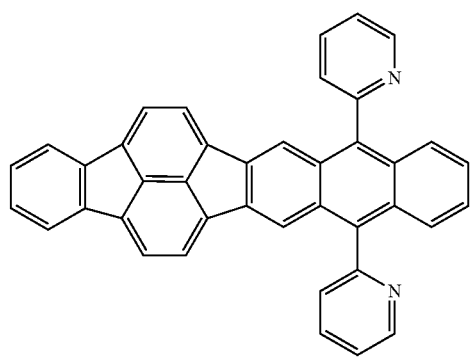
B4
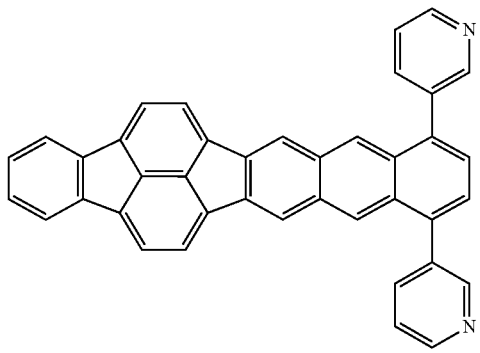
B5
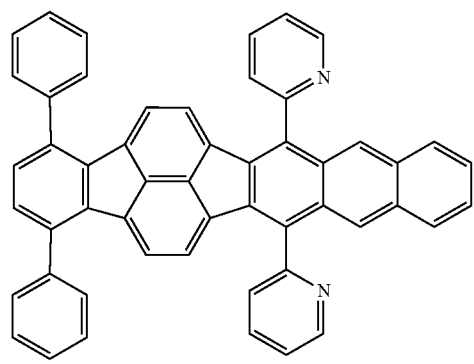
B6
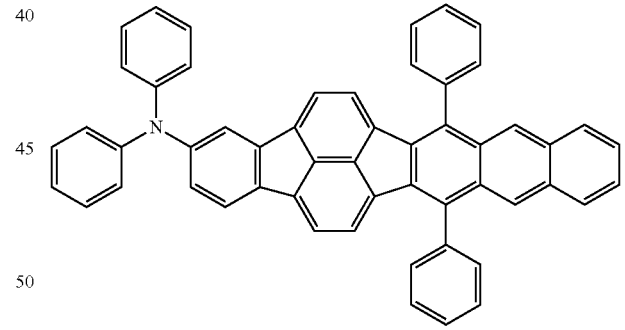
B7
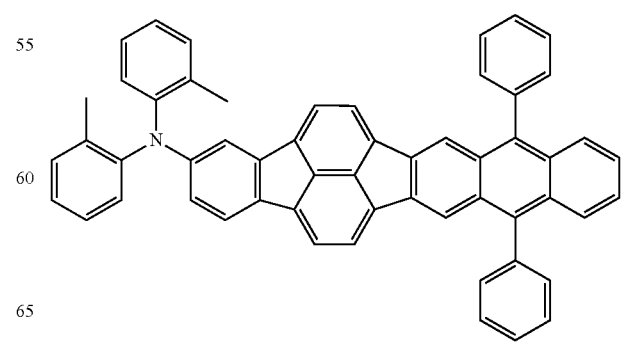

B8
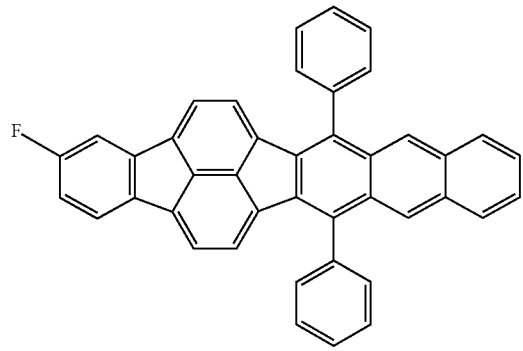
B9
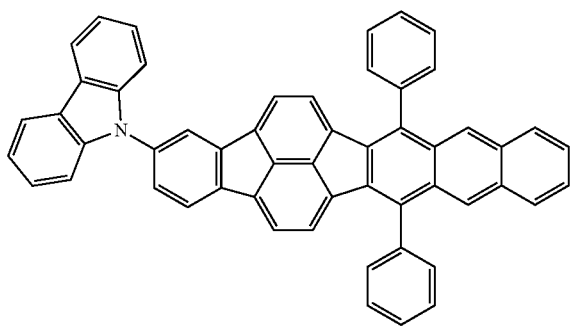
B10
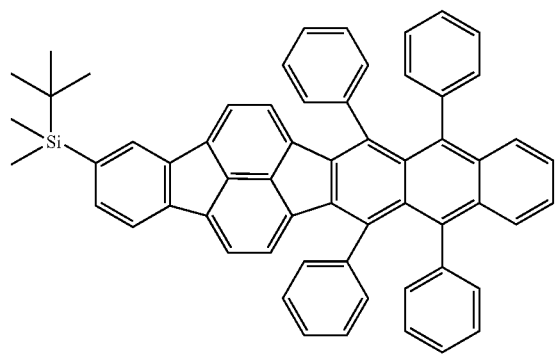
B11
B12
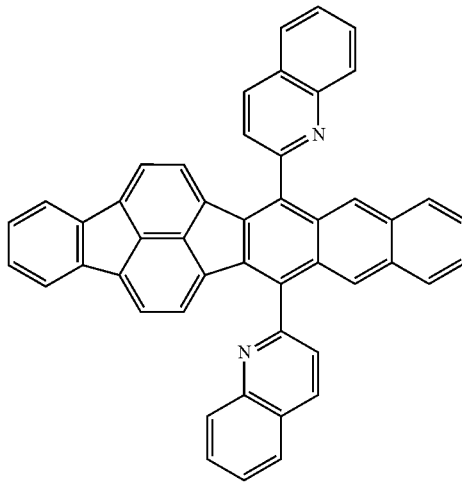
B13
B14
B15
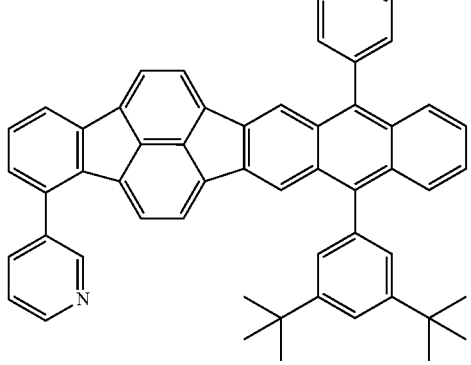

B16

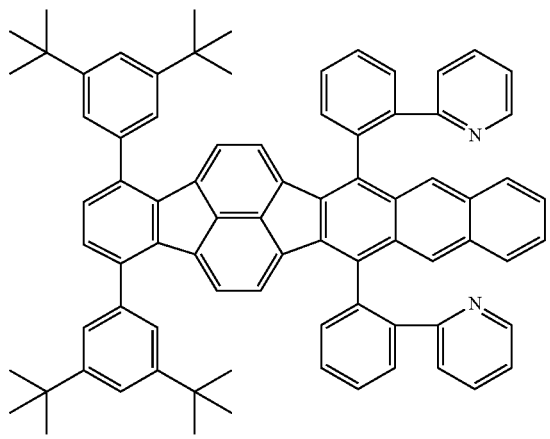

B19

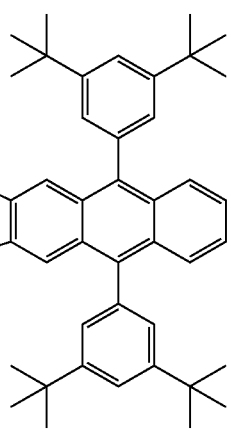

B17

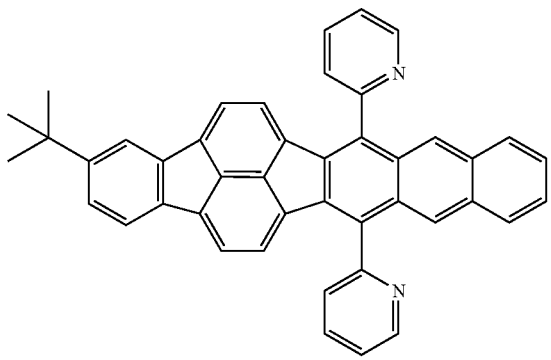

B20

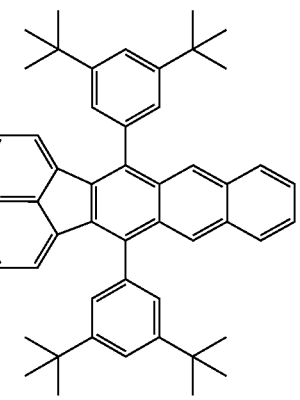

B18

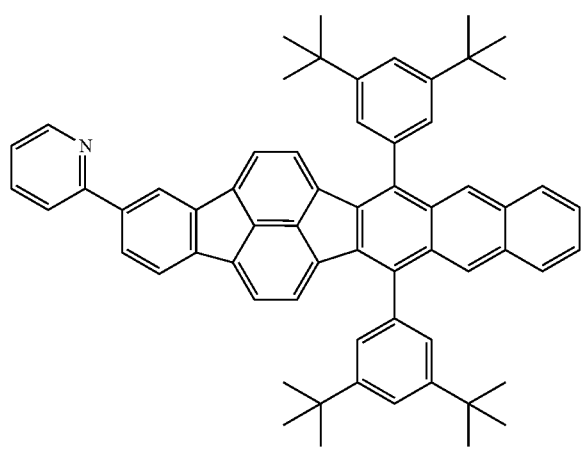

Properties of Groups of Exemplary Compounds

Of the exemplary compounds, those in Group A have a low HOMO energy level because the entire molecule, rather than only the basic backbone, is composed only of hydrocarbon groups. This means that these organic compounds have low oxidation potential and are therefore stable to oxidation.

On the other hand, if any substituent has a heteroatom, as in Group B, the oxidation potential of the molecule varies considerably, or the intermolecular interaction varies. If any substituent has a heteroatom, it can make the maximum emission wavelength longer. In addition, if any substituent has a heteroatom, the compound can be used, for example, for applications where it is used in a high concentration approaching 100% as an electron transport material, a hole transport material, or a hole-trap light-emitting material.

Thus, exemplary compounds are shown as Groups A and B. These compounds emit green light only with the basic backbone thereof. Furthermore, the organic compound according to this embodiment can emit light having a longer wavelength than green light, specifically, red light, if the basic backbone thereof is substituted.

In particular, the organic compound according to this embodiment can be represented by general formula (2):

[Chem. 12]

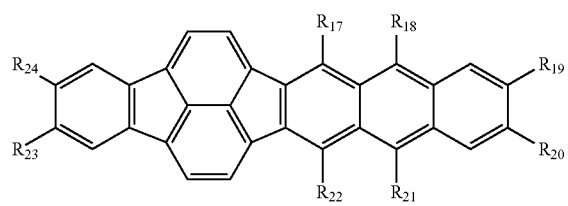
(2)

In general formula (2), $R_{17}$ to $R_{24}$ are each independently selected from an alkyl group having one to four carbon atoms and an aryl group.

The aryl group is phenyl, naphthyl, biphenyl, or terphenyl.

The aryl group can be substituted with an alkyl group having one to four carbon atoms.

If any of $R_{17}$, $R_{18}$, $R_{21}$, and $R_{22}$ is an aryl group, it makes a large dihedral angle with the basic backbone of the organic compound according to this embodiment.

This inhibits molecular stacking, thus providing a great effect of inhibiting concentration quenching.

If $R_{19}$, $R_{20}$, $R_{23}$, or $R_{24}$ is a substituent, it can make the emission wavelength longer. If the substituent is an aryl group, it can make the emission wavelength even longer.

Description of Synthesis Route

An example of the synthesis route of the organic compound according to this embodiment will now be described. The reaction formulas are shown below.

To synthesize a compound having a substituent introduced to an intended position, the hydrogen atom at the intended position can be substituted with another substituent. Examples of substituents include an alkyl group, a halogen atom, and a phenyl group.

Synthesis route 1

[Chem. 13]

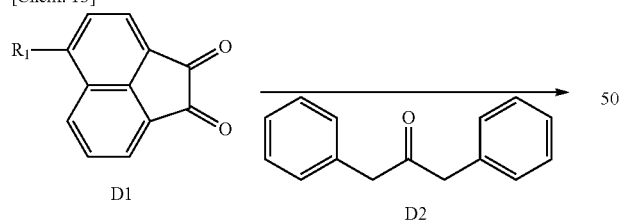

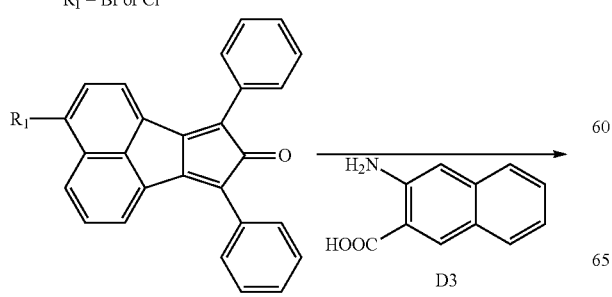

-continued

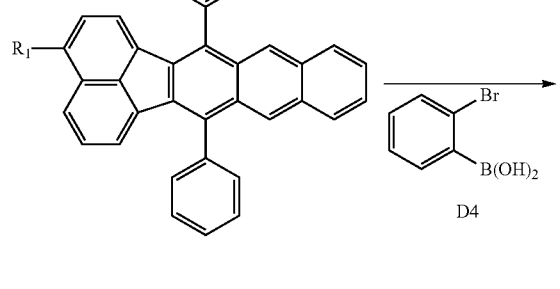

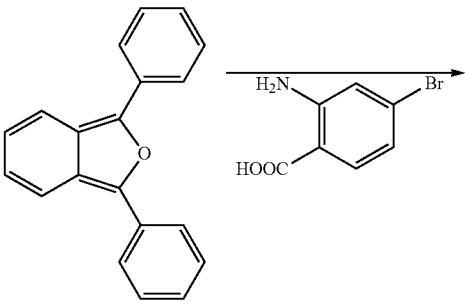

Synthesis route 2

[Chem. 14]

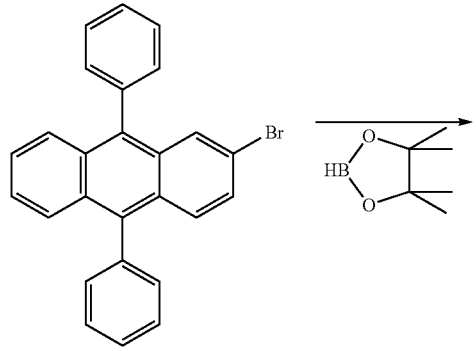

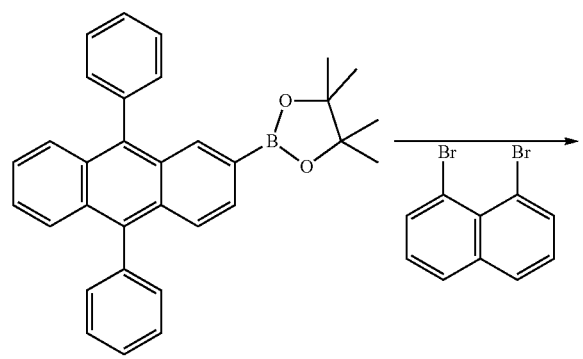

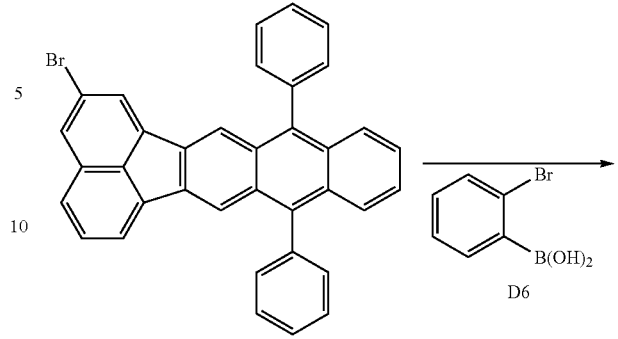

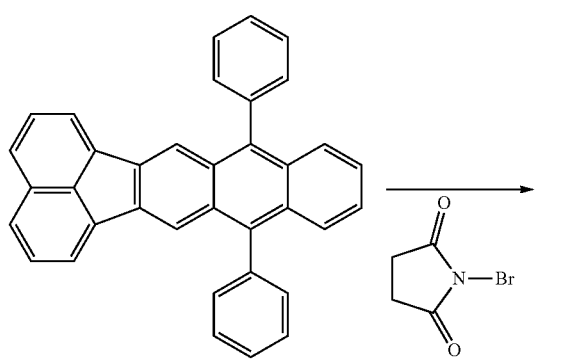

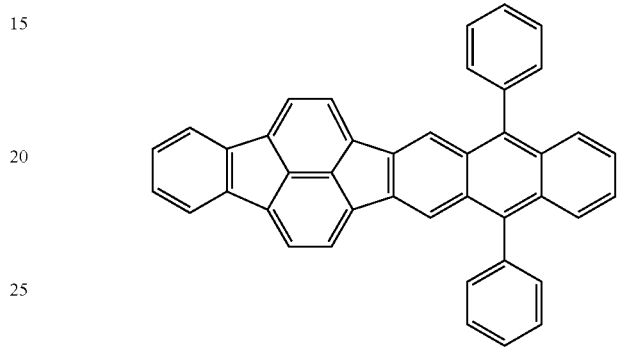

Other Organic Compounds and Raw Materials

Various organic compounds can be synthesized by changing D1 to D6 in the above reaction formulas. Tables 2 and 3 show examples of compounds synthesized.

TABLE 2

| Example No. | D1 or D5 | D2 | D3 |
|---|---|---|---|
| 1 | ![R1-acenaphthylenedione] | ![dibenzyl ketone with biphenyl groups] | ![3-amino-2-naphthoic acid] |
| 2 | ![R1-acenaphthylenedione] | ![dibenzyl ketone with phenyl groups] | ![3-amino-2-naphthoic acid] |
| 3 | ![R1-acenaphthylenedione] | ![di(3,5-di-tert-butylbenzyl) ketone] | ![3-amino-2-naphthoic acid] |

TABLE 2-continued
| 4 | 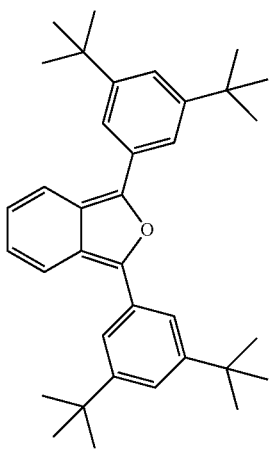 | — | 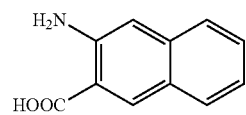 |
| 5 | 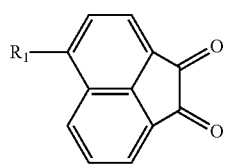 | 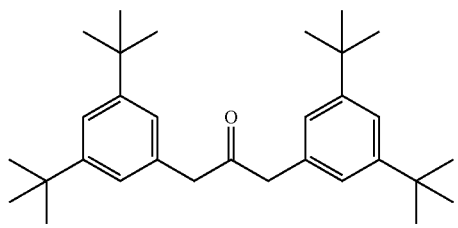 | 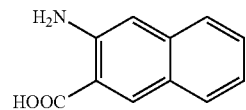 |
| 6 | 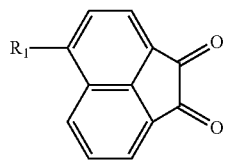 | 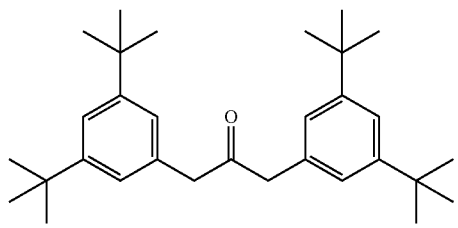 | 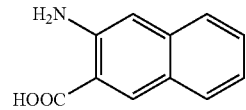 |
| 7 | 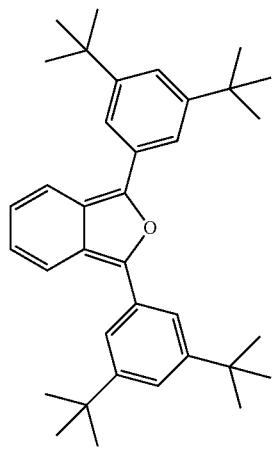 [SMILES: CC(C)(C)c1cc(-c2oc(-c3cc(C(C)(C)C)cc(C(C)(C)C)c3)c3ccccc23)cc(C(C)(C)C)c1] | — | — |

TABLE 2-continued

| Example No. | D4 or D6 | Compound synthesized | Exemplary compound No. |
|---|---|---|---|
| 1 | (2-bromophenyl)boronic acid | (structure) | A13 |
| 2 | 2-bromo-[1,1':4',1''-terphenyl]-3'-ylboronic acid | (structure) | A16 |
| 3 | (2-bromophenyl)boronic acid | (structure) | A22 |

TABLE 2-continued
| 4 | 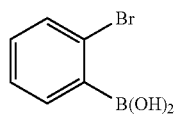 | 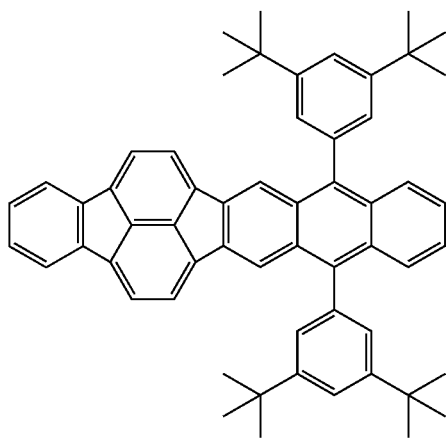 [SMILES: CC(C)(C)c1cc(-c2c3ccccc3c(-c3cc(C(C)(C)C)cc(C(C)(C)C)c3)c3cc4c(cc23)-c2ccc3c5c(ccc-4c25)-c2ccccc2-3)cc(C(C)(C)C)c1] | A23 |
| 5 | 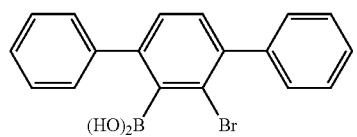 [SMILES: OB(O)c1c(-c2ccccc2)ccc(-c2ccccc2)c1Br] | 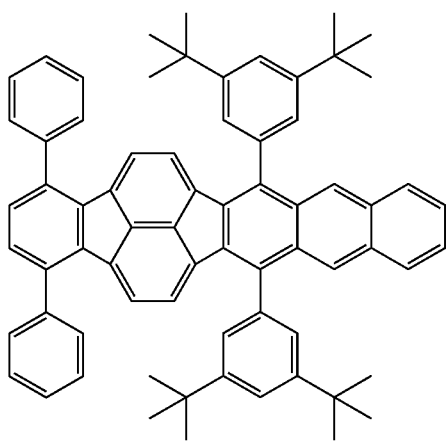 [SMILES: CC(C)(C)c1cc(-c2c3c(c(-c4cc(C(C)(C)C)cc(C(C)(C)C)c4)c4cc5ccccc5cc24)-c2ccc4c5c(ccc-3c25)-c2c(-c3ccccc3)ccc(-c3ccccc3)c2-4)cc(C(C)(C)C)c1] | A24 |
| 6 | 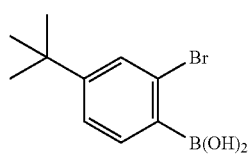 | 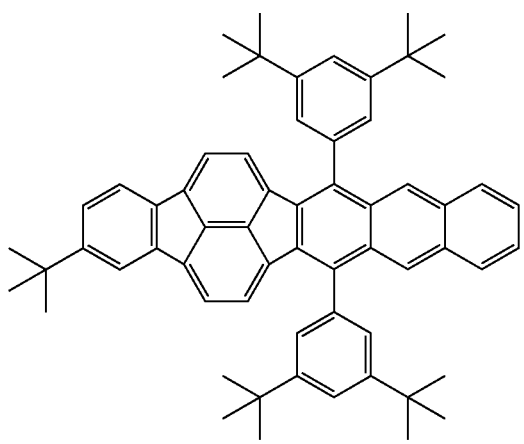 [SMILES: CC(C)(C)c1cc(-c2c3c(c(-c4cc(C(C)(C)C)cc(C(C)(C)C)c4)c4cc5ccccc5cc24)-c2ccc4c5c(ccc-3c25)-c2ccc(C(C)(C)C)cc2-4)cc(C(C)(C)C)c1] | A25 |

TABLE 2-continued
| 7 | 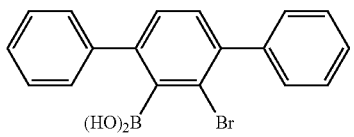 [SMILES: OB(O)c1c(-c2ccccc2)ccc(-c2ccccc2)c1Br] | 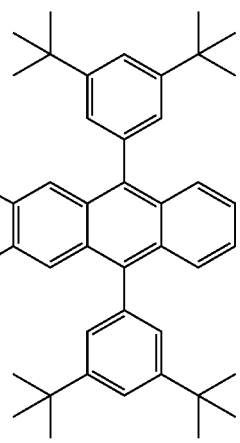 | A27 |
TABLE 3
| Example No. | D1 or D5 | D2 | D3 |
|---|---|---|---|
| 8 | | | |
| 9 | | | |
| 10 | | | |
| 11 | | | |
| 12 | | | |
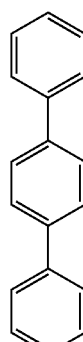

TABLE 3-continued
| 13 | 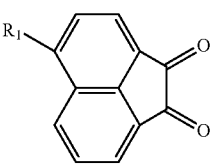 | 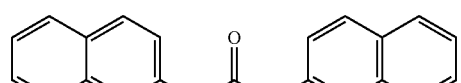 | 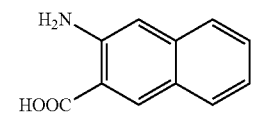 |
| 14 | 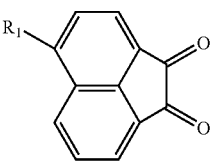 | 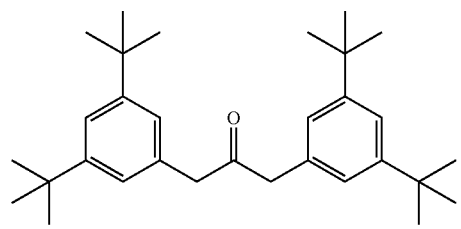 | 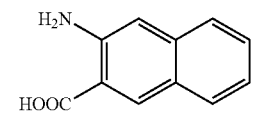 |
| Example No. | D4 or D6 | Compound synthesized | Exemplary compound No. |
|---|---|---|---|
| 8 | 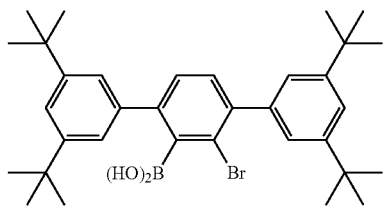 [SMILES: CC(C)(C)c1cc(-c2ccc(-c3cc(C(C)(C)C)cc(C(C)(C)C)c3)c(B(O)O)c2Br)cc(C(C)(C)C)c1] | 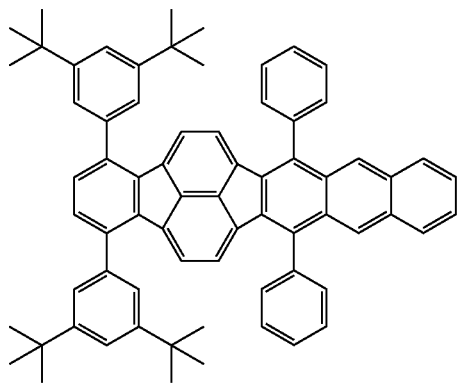 [SMILES: CC(C)(C)c1cc(-c2ccc(-c3cc(C(C)(C)C)cc(C(C)(C)C)c3)c3c2-c2ccc4c5c(ccc-3c25)-c2c-4c(-c3ccccc3)c3cc4ccccc4cc3c2-c2ccccc2)cc(C(C)(C)C)c1] | A30 |
| 9 | 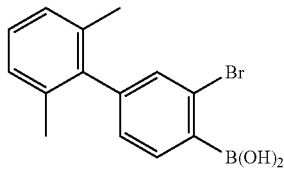 [SMILES: Cc1cccc(C)c1-c1ccc(B(O)O)c(Br)c1] | 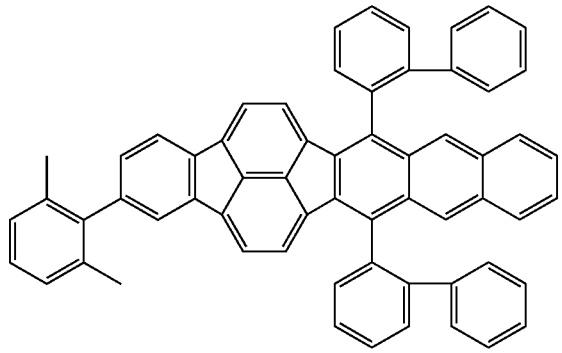 [SMILES: Cc1cccc(C)c1-c1ccc2c(c1)-c1ccc3c4c(ccc-2c14)-c1c-3c(-c2ccccc2-c2ccccc2)c2cc3ccccc3cc2c1-c1ccccc1-c1ccccc1] | A32 |

US 9,145,344 B2
41                                                42
TABLE 3-continued
| 10 | 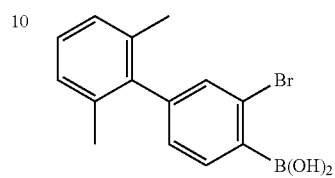 | 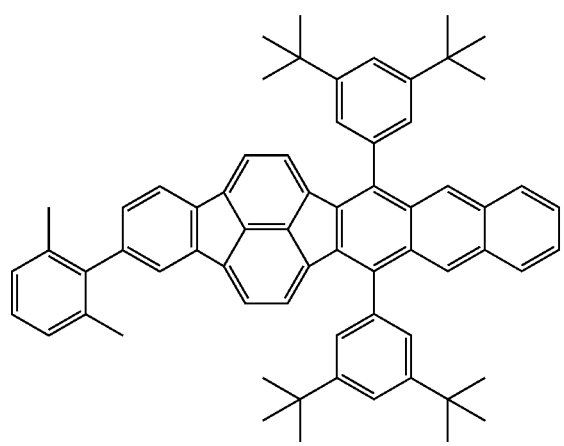 [SMILES: Cc1cccc(C)c1-c1ccc2c(c1)-c1ccc3c4c(ccc-2c14)-c1c-3c(-c2cc(C(C)(C)C)cc(C(C)(C)C)c2)c2cc3ccccc3cc2c1-c1cc(C(C)(C)C)cc(C(C)(C)C)c1] | A44 |
| 11 | 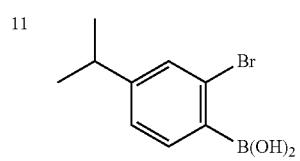 | 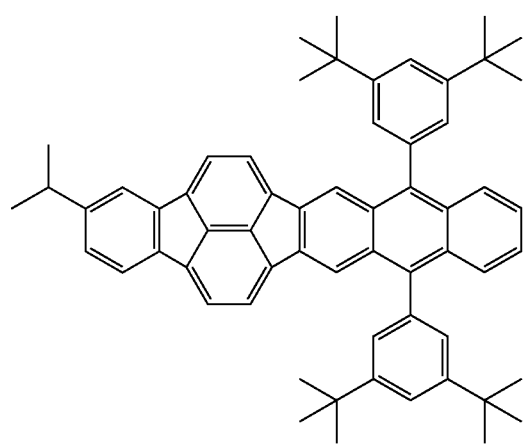 [SMILES: CC(C)c1ccc2c(c1)-c1ccc3c4c(ccc-2c14)-c1cc2c(-c4cc(C(C)(C)C)cc(C(C)(C)C)c4)c4ccccc4c(-c4cc(C(C)(C)C)cc(C(C)(C)C)c4)c2cc1-3] | A46 |
| 12 | 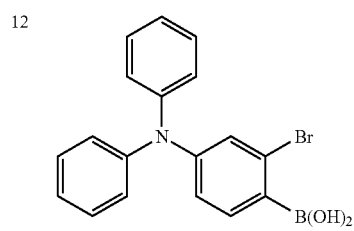 | 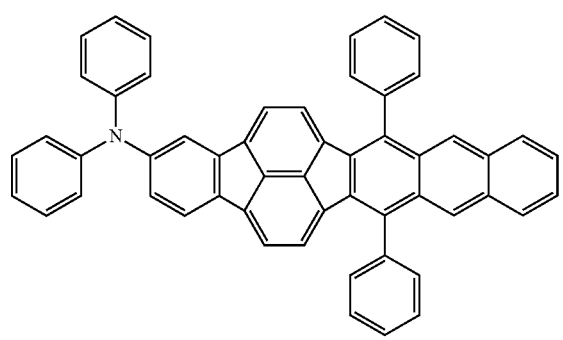 [SMILES: c1ccc(-c2c3c(c(-c4ccccc4)c4cc5ccccc5cc24)-c2ccc4c5c(ccc-3c25)-c2ccc(N(c3ccccc3)c3ccccc3)cc2-4)cc1] | B6 |

TABLE 3-continued

13 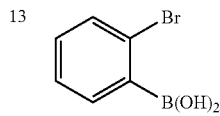

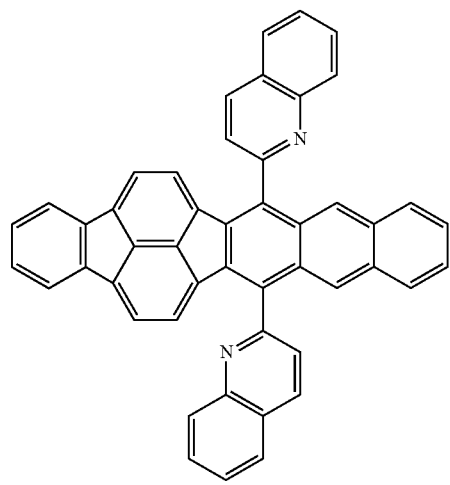 [SMILES: c1ccc2c(c1)-c1ccc3c4c(ccc-2c14)-c1c-3c(-c2ccc3ccccc3n2)c2cc3ccccc3cc2c1-c1ccc2ccccc2n1]
B14

14 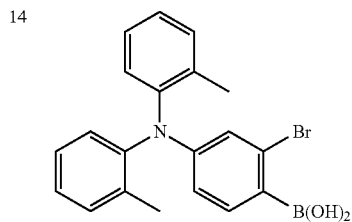

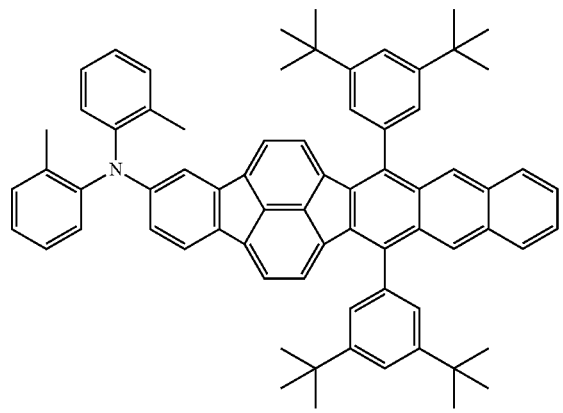 [SMILES: Cc1ccccc1N(c1ccc2c(c1)-c1ccc3c4c(ccc-2c14)-c1c-3c(-c2cc(C(C)(C)C)cc(C(C)(C)C)c2)c2cc3ccccc3cc2c1-c1cc(C(C)(C)C)cc(C(C)(C)C)c1)c1ccccc1C]
B20

Description of Organic Light-Emitting Device

Next, an organic light-emitting device according to an embodiment of the present invention will be described.

The organic light-emitting device according to this embodiment includes at least a pair of electrodes, namely, an anode and a cathode, and an organic compound layer disposed therebetween. The organic compound layer contains an organic compound according to the present invention.

If the organic compound layer is a light-emitting layer, it can be formed only of the organic compound according to the present invention or can contain another component.

The case where the light-emitting layer contains another component means the case where the light-emitting layer contains a host material or an assist material as well as the component responsible for emitting light. The organic compound according to the present invention can be a host material, a guest material, or an assist material.

If the organic compound according to the present invention is used as a guest material, the concentration of the guest material in the host material is preferably 0.01% to 20% by weight, more preferably 0.5% to 10% by weight.

As a result of various research, the present inventors have found that a device formed using an organic compound according to the present invention as a host or guest material of a light-emitting layer, particularly as a guest material, provides optical output with high efficiency and high luminance and has extremely high durability.

Examples of organic light-emitting devices using organic compounds according to this embodiment will now be described.

An example of an organic light-emitting device according to this embodiment is one including a substrate on which an anode, a light-emitting layer, and a cathode are disposed in the above order. Another example is one including an anode, a hole transport layer, an electron transport layer, and a cathode disposed in the above order. Other examples include one including an anode, a hole transport layer, a light-emitting layer, an electron transport layer, and a cathode disposed in the above order; one including an anode, a hole injection layer, a hole transport layer, a light-emitting layer, an electron transport layer, and a cathode disposed in the above order; and one including an anode, a hole transport layer, a light-emitting layer, a hole/exciton blocking layer, an electron transport layer, and a cathode disposed in the above order. These examples, however, are merely basic device structures, and the structures of organic light-emitting devices according to this embodiment are not limited thereto; various layer structures can be employed, including, for example, one including an insulating layer at the interface between an electrode and the organic compound layer, one including an adhesive layer or an interfering layer, and one including an electron or hole transport layer composed of two layers with different ionization potentials.

In addition to the organic compound according to the present invention, other compounds can be optionally used, including a known low-molecular-weight or polymer hole injection compound or hole transport compound, a known low-molecular-weight or polymer host compound or luminescent compound (host material), and a known low-molecular-weight or polymer electron injection compound or electron transport compound.

Examples of such compounds are shown below.

The hole injection compound or hole transport compound used can be a material having high hole mobility. Example of low-molecular-weight or polymer materials with hole injection properties or hole transport properties include, but not limited to, triarylamines, phenylenediamines, stilbenes, phthalocyanines, porphyrins, polyvinylcarbazole, polythiophene, and other conductive polymers.

Table 4 shows specific structural formulae of host compounds. As the host compound, derivatives having the structural formulae shown in Table 4 can be used. Other examples include, but not limited to, fused ring compounds (such as fluorenes, naphthalenes, anthracenes, pyrenes, carbazoles, quinoxalines, and quinolines), organoaluminum complexes such as tris(8-quinolinolato)aluminum, organozinc complexes, triphenylamines, and polymers such as polyfluorenes and polyphenylenes.

TABLE 4

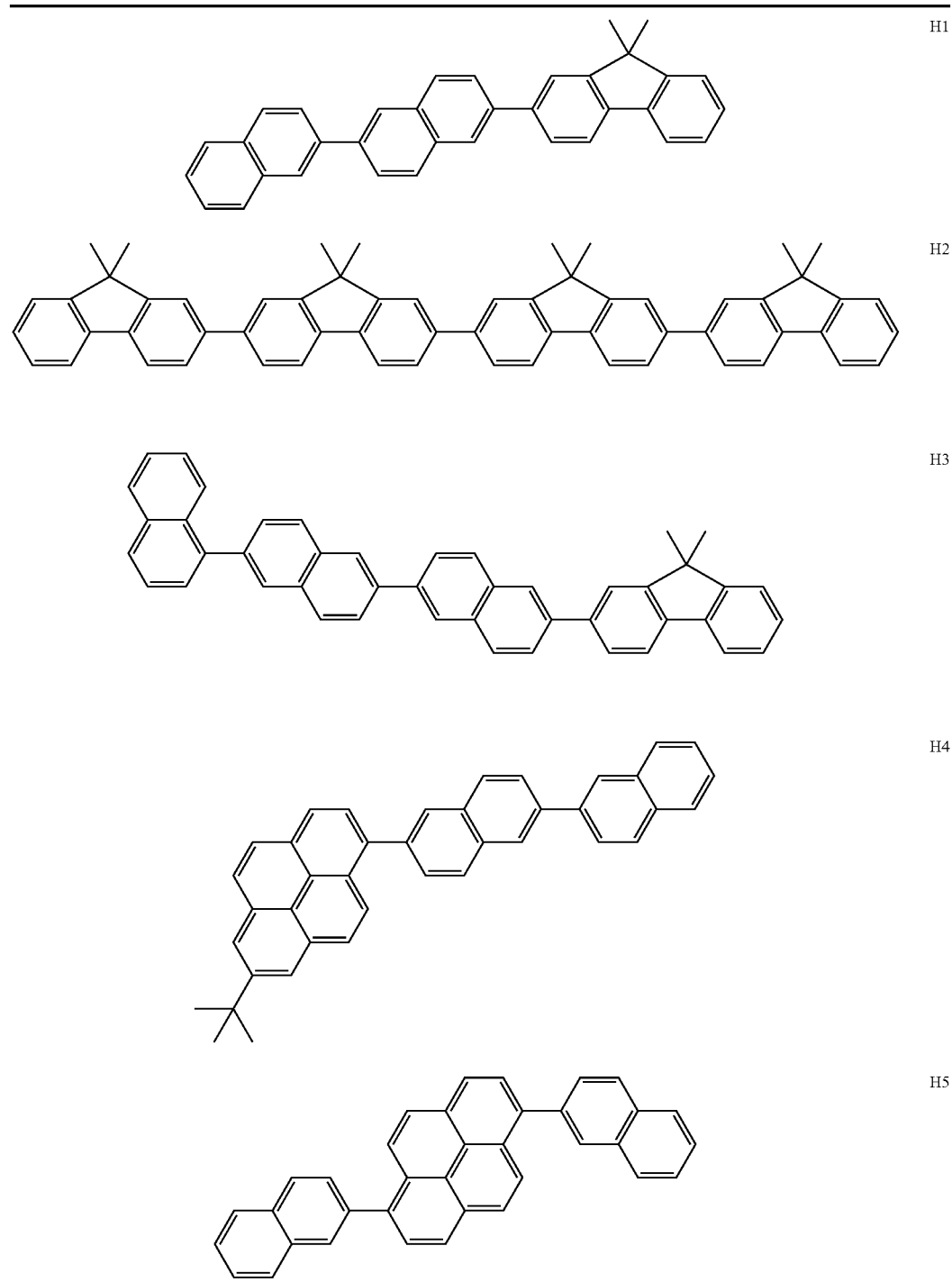

TABLE 4-continued
| | |
|---|---|
| 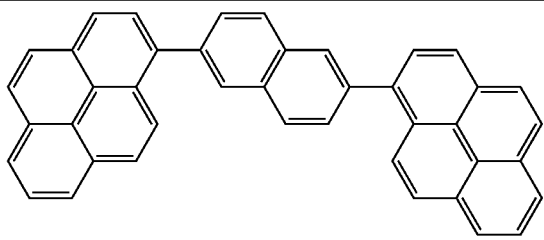 | H6 |
| 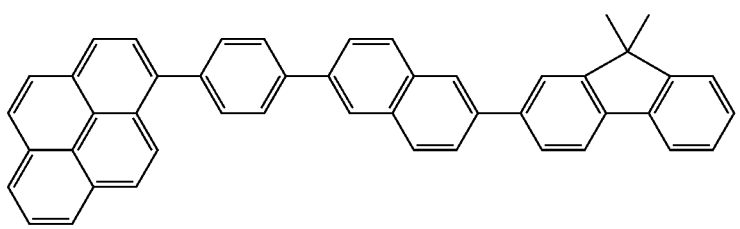 [SMILES: CC1(C)c2ccccc2-c2ccc(-c3ccc4cc(-c5ccc(-c6ccc7ccc8cccc9ccc6c7c89)cc5)ccc4c3)cc21] | H7 |
| 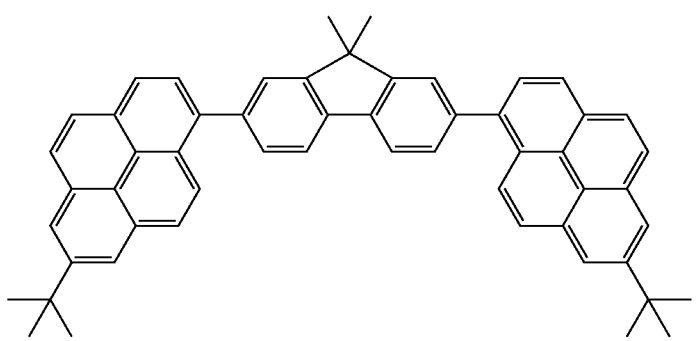 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34] | H8 |
| 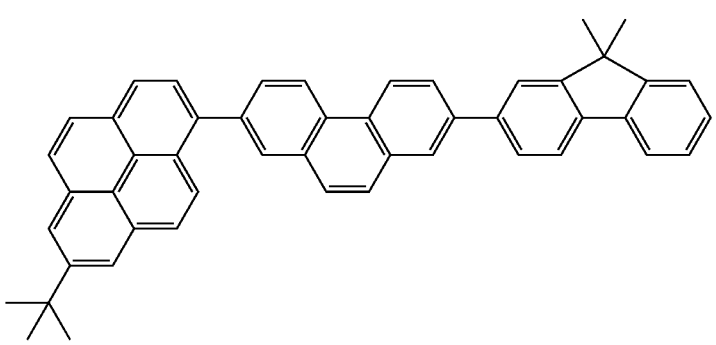 [SMILES: CC(C)(C)c1cc2ccc3ccc(-c4ccc5c(ccc6cc(-c7ccc8c(c7)C(C)(C)c7ccccc7-8)ccc65)c4)c4ccc(c1)c2c34] | H9 |
| 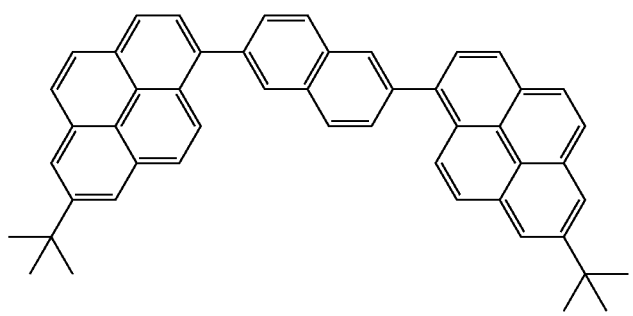 [SMILES: CC(C)(C)c1cc2ccc3ccc(-c4ccc5cc(-c6ccc7ccc8cc(C(C)(C)C)cc9ccc6c7c89)ccc5c4)c4ccc(c1)c2c34] | H10 |

TABLE 4-continued
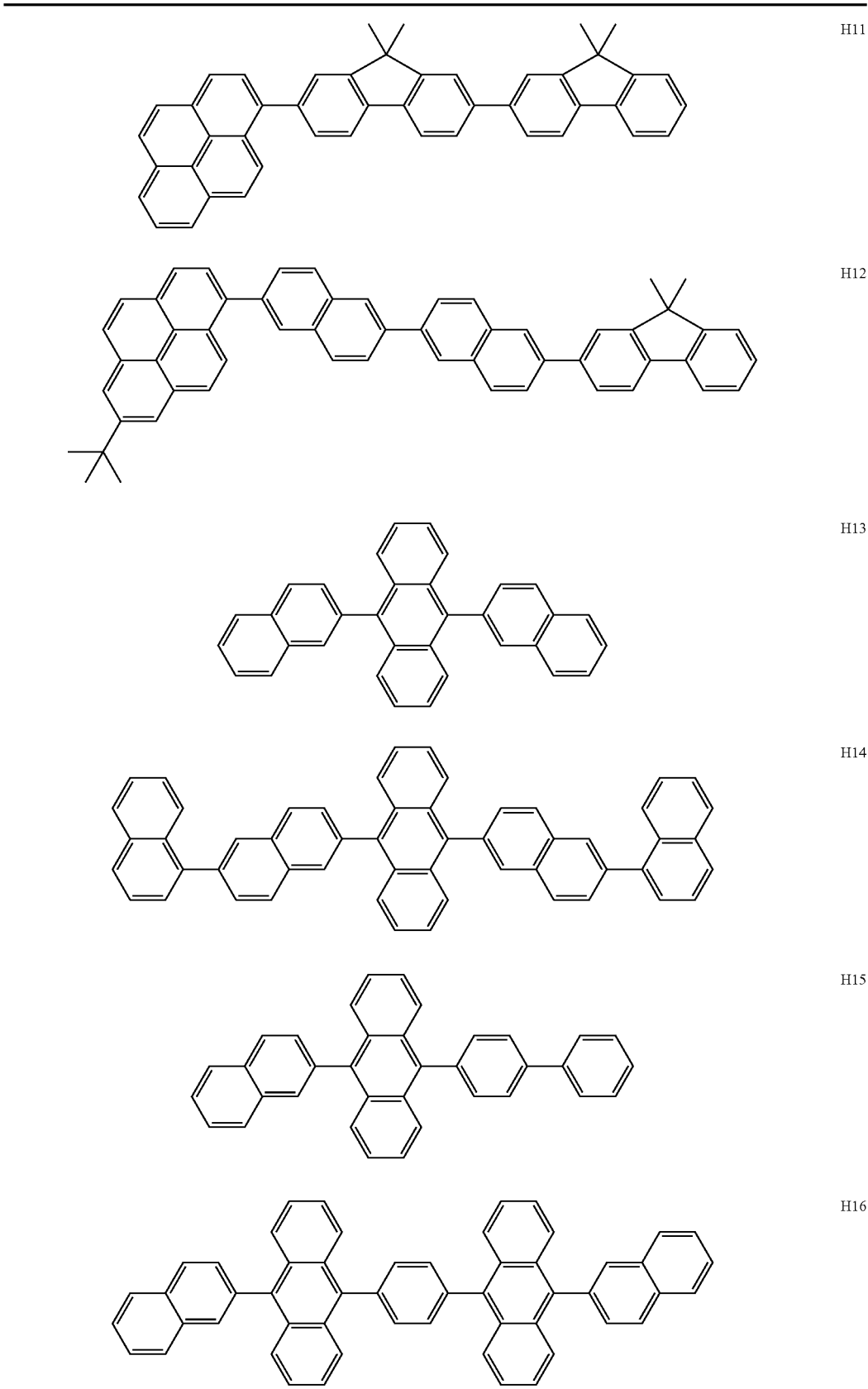
H11
H12
H13
H14
H15
H16

TABLE 4-continued
| | |
|---|---|
| 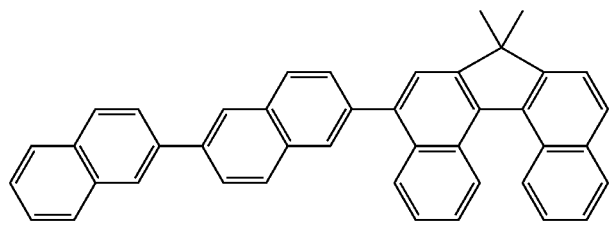 [SMILES: CC1(C)c2ccc3ccccc3c2-c2c1cc(-c1ccc3cc(-c4ccc5ccccc5c4)ccc3c1)c1ccccc21] | H17 |
| 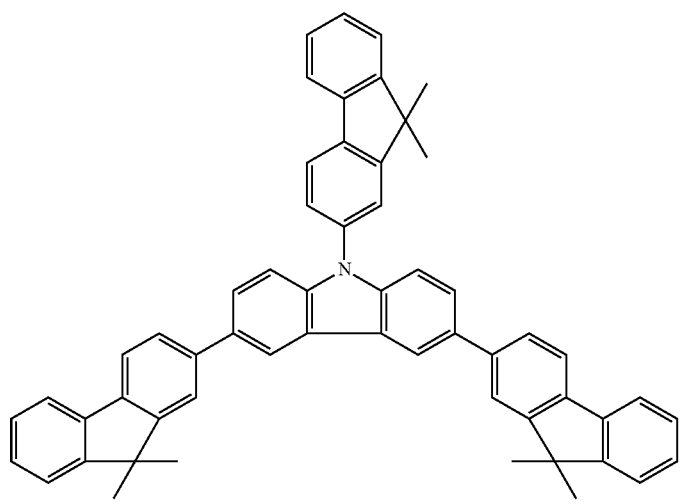 [SMILES: CC1(C)c2ccccc2-c2ccc(-c3ccc4c(c3)c3cc(-c5ccc6c(c5)C(C)(C)c5ccccc5-6)ccc3n4-c3ccc4c(c3)C(C)(C)c3ccccc3-4)cc21] | H18 |
| 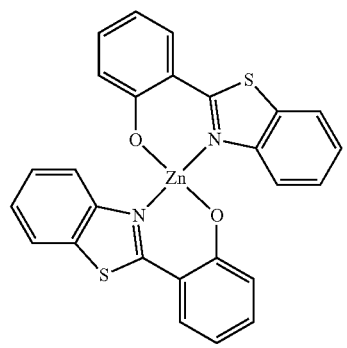 | H19 |
| 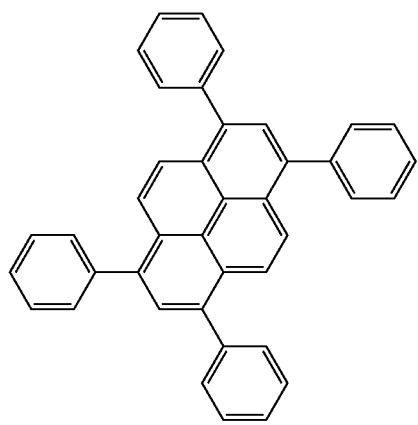 [SMILES: c1ccc(-c2cc(-c3ccccc3)c3ccc4c(-c5ccccc5)cc(-c5ccccc5)c5ccc2c3c54)cc1] | H20 |

TABLE 4-continued
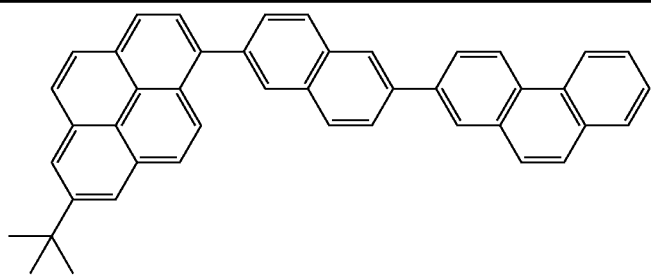 H21
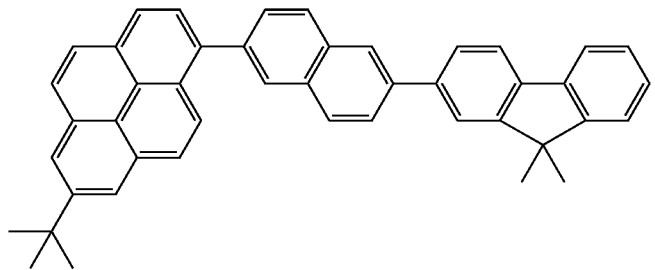 [SMILES: CC(C)(C)c1cc2ccc3ccc(-c4ccc5cc(-c6ccc7c(c6)C(C)(C)c6ccccc6-7)ccc5c4)c4ccc(c1)c2c34] H22
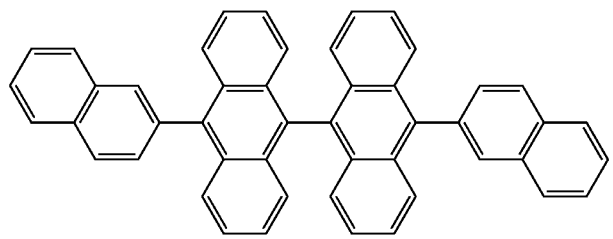 [SMILES: c1ccc2cc(-c3c4ccccc4c(-c4c5ccccc5c(-c5ccc6ccccc6c5)c5ccccc45)c4ccccc34)ccc2c1] H23
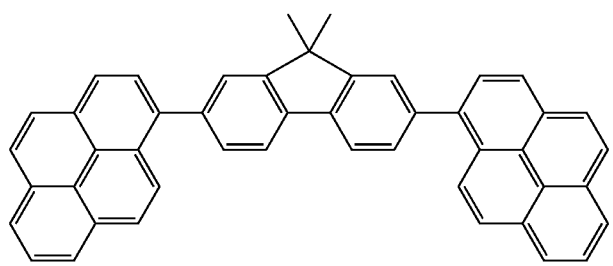 [SMILES: CC1(C)c2cc(-c3ccc4ccc5cccc6ccc3c4c56)ccc2-c2ccc(-c3ccc4ccc5cccc6ccc3c4c56)cc21] H24
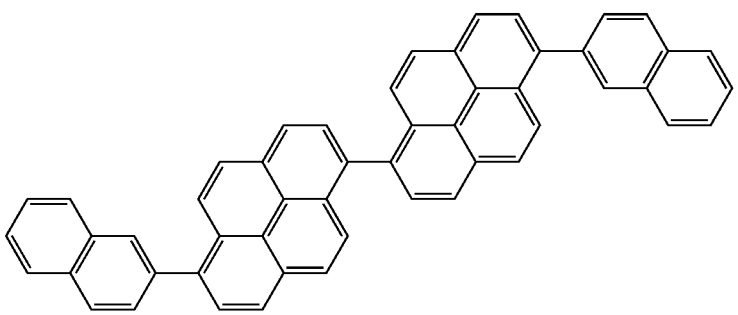 [SMILES: c1ccc2cc(-c3ccc4ccc5c(-c6ccc7ccc8c(-c9ccc%10ccccc%10c9)ccc9ccc6c7c98)ccc6ccc3c4c65)ccc2c1] H25
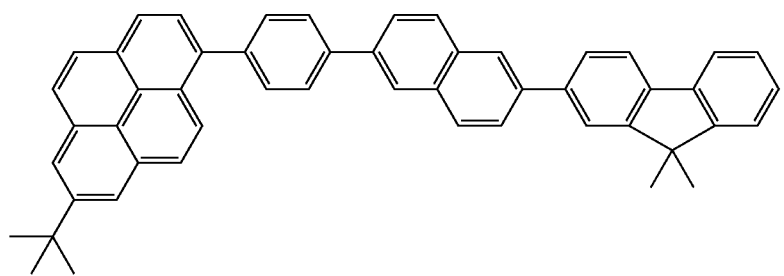 [SMILES: CC(C)(C)c1cc2ccc3ccc(-c4ccc(-c5ccc6cc(-c7ccc8c(c7)C(C)(C)c7ccccc7-8)ccc6c5)cc4)c4ccc(c1)c2c34] H26

TABLE 4-continued

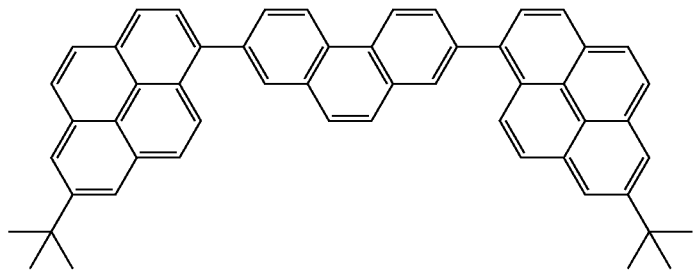 [SMILES: CC(C)(C)c1cc2ccc3ccc(-c4ccc5c(ccc6cc(-c7ccc8ccc9cc(C(C)(C)C)cc%10ccc7c8c9%10)ccc65)c4)c4ccc(c1)c2c34]

H27

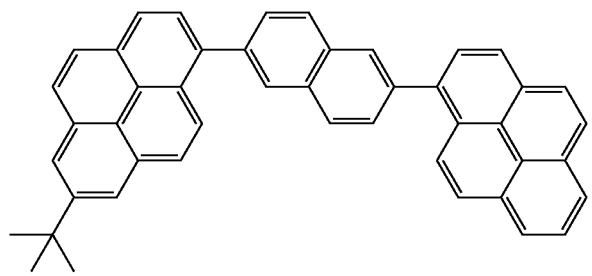 [SMILES: CC(C)(C)c1cc2ccc3ccc(-c4ccc5cc(-c6ccc7ccc8cccc9ccc6c7c89)ccc5c4)c4ccc(c1)c2c34]

H28

The electron injection compound or electron transport compound used is selected taking into account, for example, the balance against the hole mobility of the hole injection compound or hole transport compound. Examples of compounds with electron injection properties or electron transport properties include, but not limited to, oxadiazoles, oxazoles, pyrazines, triazoles, triazines, quinolines, quinoxalines, phenanthrolines, and organoaluminum complexes.

The anode material used can be a material having a higher work function. Examples of such materials include metals such as gold, platinum, silver, copper, nickel, palladium, cobalt, selenium, vanadium, and tungsten and alloys thereof and metal oxides such as tin oxide, zinc oxide, indium oxide, indium tin oxide (ITO), and indium zinc oxide (IZO). Conductive polymers such as polyaniline, polypyrrole, and polythiophene can also be used. These electrode materials can be used alone or in combination. The anode can have either a monolayer structure or a multilayer structure.

On the other hand, the cathode material used can be a material having a lower work function. Examples of such materials include alkali metals such as lithium; alkaline earth metals such as calcium; and metals such as aluminum, titanium, manganese, silver, lead, and chromium. Alloys of these metals can also be used, including magnesium-silver, aluminum-lithium, and aluminum-magnesium. In addition, metal oxides such as ITO can be used. These electrode materials can be used alone or in combination. The cathode can have either a monolayer structure or a multilayer structure.

In the organic light-emitting device according to this embodiment, the layer containing the organic compound according to the present invention and the other organic compound layers are typically formed by vacuum deposition, ion-assisted deposition, sputtering, plasma-assisted deposition, or a known coating process for forming a thin film using an appropriate solvent (such as spin coating, dipping, casting, the Langmuir-Blodgett (LB) technique, or inkjet coating). If the layers are formed by vacuum deposition or solution coating, they have superior stability over time because, for example, crystallization does not tend to occur. If the layers are formed by coating, films can be formed in combination with an appropriate binder resin.

Examples of binder resins include, but not limited to, polyvinylcarbazole resins, polycarbonate resins, polyester resins, acrylonitrile-butadiene-styrene (ABS) resins, acrylic resins, polyimide resins, phenolic resins, epoxy resins, silicone resins, and urea resins. These binder resins can be used alone as a homopolymer or copolymer or can be used as a mixture of two or more. In addition, known additives such as a plasticizer, an antioxidant, and an ultraviolet absorber can be optionally used in combination.

Display Apparatus Including Organic Light-Emitting Devices

Apparatuses including organic light-emitting devices according to this embodiment will now be described.

An organic light-emitting device according to this embodiment can be used for a display apparatus or an illumination apparatus. Other applications include exposure light sources for electrophotographic image-forming apparatuses and backlights for liquid-crystal display apparatuses.

The display apparatus includes a display unit including organic light-emitting devices according to this embodiment. The display unit has a plurality of pixels. The pixels include the organic light-emitting devices according to this embodiment and thin-film transistors (TFTs), which serve as an example of switching devices. The anodes or cathodes of the organic light-emitting devices are connected to the drains or sources of the TFTs. The display apparatus can be used as, for example, an image display apparatus for personal computers. The display apparatus can also be configured as an image input apparatus further including an image input unit.

The image input apparatus includes an image input unit configured to input information from, for example, an area charge-coupled device (CCD) sensor, a linear CCD sensor, or a memory card and a display unit configured to display the input information. The image input apparatus can also be configured as an image pickup apparatus, such as a digital camera, further including an image pickup optical system. For an image pickup apparatus or inkjet printer, the display apparatus can have both the image output function of display ing an image on the basis of image information input from outside to serve as a display unit and the input function of inputting information on the basis of which the image is processed to serve as a control panel. The display apparatus can also be used as a display unit of a multifunction printer.

Next, a display apparatus including organic light-emitting devices according to this embodiment will be described.

FIG. 1 is a schematic sectional view of the organic light-emitting devices according to this embodiment and TFTs, which serve as an example of switching devices for controlling the on/off or luminous intensity of the organic light-emitting devices. FIG. 1 illustrates two pairs of organic light-emitting devices and TFTs. Although not shown, the display apparatus can include transistors for controlling the luminous intensity. The display apparatus displays information by switching on and off the organic light-emitting devices by driving the switching devices on the basis of the information. The detailed structure will now be described.

The display apparatus in FIG. 1 includes a substrate 1, such as a glass substrate, and a moisture-proofing film 2, disposed over the substrate 1, for protecting TFTs 8 and organic compound layers 12, and also includes metal gates 3, gate insulators 4, and semiconductor layers 5.

The TFTs 8 include the semiconductor layers 5, drains 6, and sources 7. An insulating film 9 is disposed over the TFTs 8. Anodes 11 of the organic light-emitting devices are connected to the sources 7 via contact holes 10. The structure of the display apparatus is not limited to the above structure, but can be any structure in which either the anodes 11 or the cathodes 13 are connected to either the sources 7 or the drains 6 of the TFTs 8.

The organic compound layers 12 are each composed of a plurality of organic compound layers, although they are shown as single layers in FIG. 1 for illustration purposes. A first protective layer 14 and a second protective layer 15 are disposed over the cathodes 13 to inhibit degradation of the organic light-emitting devices.

The switching devices of the display apparatus according to this embodiment can be of any type. For example, single-crystal silicon substrates, metal-insulator-metal (MIM) devices, or amorphous silicon (a-Si) devices can be used.

EXAMPLES

Example 1

Synthesis of Exemplary Compound A2

[Chem. 15]

Put in 200 mL of ethanol were 10.6 g (50 mmol) of E1 and 10.5 g (50 mmol) of E2. After the solution was heated to 60° C., 20 mL of 6 M aqueous sodium hydroxide solution was added dropwise. Upon completion of the addition, the solution was heated to 80° C. and was stirred for two hours. After cooling, a precipitate was filtered out, was washed with water and ethanol, and was dried by heating at 80° C. under reduced pressure to yield 18.7 g of a dark green solid of E3 (yield: 86%). Next, 8.71 g (20 mmol) of E3 and 4.49 g (24 mmol) of E4 were put in 100 mL of toluene. After the solution was heated to 80° C., 2.81 g (24 mmol) of isoamyl nitrite was gradually added dropwise, and the solution was stirred at 110° C. for three hours. After cooling, the solution was washed twice with 100 mL of water. The organic layer was washed with saturated saline and was dried over magnesium sulfate. The solution was then filtered, and the filtrate was concentrated to yield a dark brown liquid. This was purified by column chromatography (toluene/heptane, 2:3) and was recrystallized from chloroform/methanol to yield 7.47 g of a yellow crystal of E5 (yield: 70%).

[Chem.16]

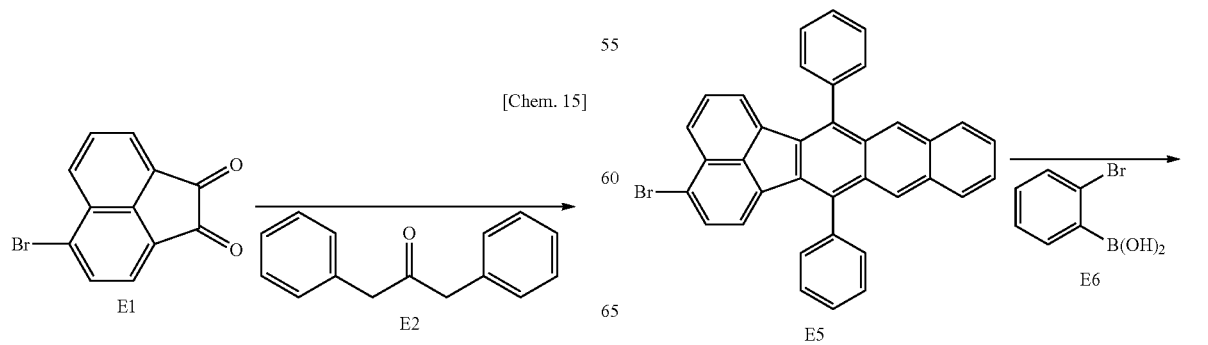

-continued

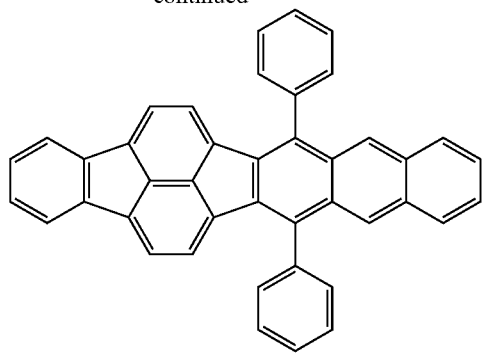

Put in 40 mL of DMF were 2.67 g (5 mmol) of E5 and 1.60 g (8 mmol) of E6. After 0.25 g (0.5 mmol) of bis(triphenylphosphine)palladium(II) dichloride and 2.28 g (15 mmol) of 1,8-diazabicyclo[5.4.0]undec-7-ene were put in the solution, it was heated to 150° C. and was stirred for four hours. After cooling, a precipitate was formed by adding 30 mL of methanol and was filtered out to yield a yellow solid. This solid was purified by column chromatography (chloroform/heptane, 1:3) and was recrystallized twice from chloroform/methanol to yield 1.77 g of a yellow crystal of exemplary compound A2 (yield: 67%).

The purity of this compound was determined to be not less than 99% by high-performance liquid chromatography (HPLC).

The emission spectrum of a toluene solution of exemplary compound A2 with a concentration of $1 \times 10^{-5}$ mol/L was measured by photoluminescence spectroscopy at an excitation wavelength of 350 nm using F-4500 available from Hitachi, Ltd. The resultant spectrum had its maximum intensity at 516 nm.

Example 2

Synthesis of Exemplary Compound A22

Exemplary compound A22 was prepared by the same reaction and purification procedure as in Example 1 except that E2, an organic compound used in Example 1, was changed to E7:

[Chem. 17]

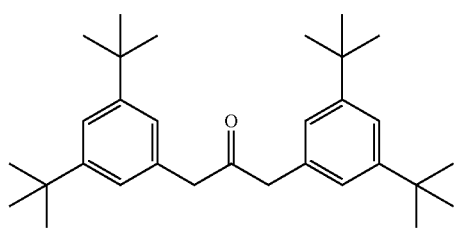

E7

The purity of this compound was determined to be not less than 99.5% by HPLC.

In addition, the structure of this compound was examined by nuclear magnetic resonance (NMR) spectroscopy.

1H NMR (CDCl$_3$, 400 MHz) σ (ppm): 8.17 (s, 2H), 7.84-7.82 (m, 2H), 7.70-7.67 (m, 2H), 7.65-7.63 (m, 2H), 7.49 (s, 2H), 7.48 (s, 2H), 7.46 (d, 2H, J=7.60 Hz), 7.39-7.37 (m, 2H), 7.21-7.17 (m, 2H), 6.40 (d, 2H, J=7.20 Hz), 1.44 (s, 36H).

The emission spectrum of a toluene solution of exemplary compound A22 with a concentration of $1 \times 10^{-5}$ mol/L was measured by photoluminescence spectroscopy at an excitation wavelength of 350 nm using F-4500 available from Hitachi, Ltd. The resultant spectrum had its maximum intensity at 517 nm.

Example 3

Synthesis of Exemplary Compound A3

[Chem. 18]

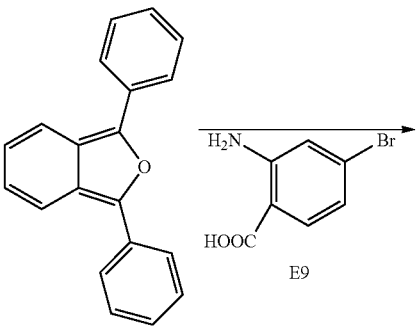

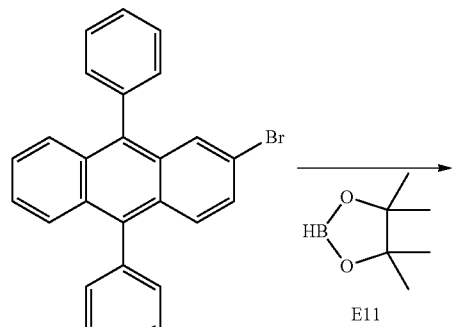

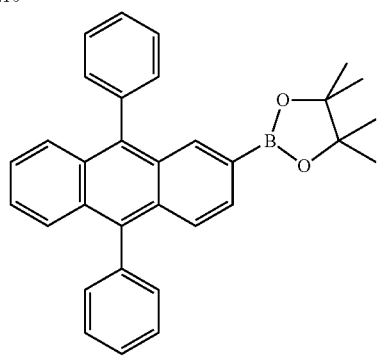

Put in 100 mL of toluene were 5.41 g (20 mmol) of E8 and 5.18 g (24 mmol) of E9. After the solution was heated to 80° C., 2.81 g (24 mmol) of isoamyl nitrite was gradually added dropwise, and the solution was gradually heated from 80° C. and was stirred at 100° C. for three hours. After cooling, the solution was washed twice with 100 mL of water. The organic layer was washed with saturated saline and was dried over magnesium sulfate. The solution was then filtered, and the filtrate was concentrated to yield a dark brown liquid. This was purified by column chromatography (toluene/heptane, 2:3) and was recrystallized from toluene/ethanol to yield 3.77 g of E10 (yield: 46%).

Next, 4.1 g (10 mmol) of E10 and 1.08 g (2 mmol) of Ni(dppp)$_2$Cl$_2$ were put in 100 mL of toluene, 3.03 g (30 mmol) of triethylamine and 3.83 g (30 mmol) of E11 were put in the solution, and it was stirred at 100° C. for five hours. After cooling, the solution was filtered and was washed twice with 100 mL of water. The organic layer was washed with saturated saline and was dried over magnesium sulfate. The solution was then filtered, and the filtrate was concentrated to yield a dark brown liquid. This was purified by column chromatography (toluene/heptane, 5:1) and was recrystallized from toluene/heptane to yield 3.19 g of E12 (yield: 70%).

solution, it was heated to 150° C. and was stirred for four hours. After cooling, a precipitate was formed by adding 30 mL of methanol and was filtered out to yield a yellow solid. This solid was purified by column chromatography (chloroform/heptane, 1:5) and was recrystallized twice from toluene/methanol to yield 3.27 g of a yellow crystal of E14 (yield: 72%). Next, 3.18 g (7 mmol) of E14 and 1.25 g (7 mmol) of E15 were put in 50 mL of chloroform, and the solution was heated to 60° C. and was stirred for eight hours. After cooling, the solution was washed twice with 50 mL of water. The organic layer was washed with saturated saline and was dried over magnesium sulfate. The solution was then filtered, and the filtrate was concentrated. This was purified by column chromatography (chloroform/heptane, 1:2) and was recrystallized from toluene/ethanol to yield 3.17 g of E16 (yield: 85%).

[Chem. 19]

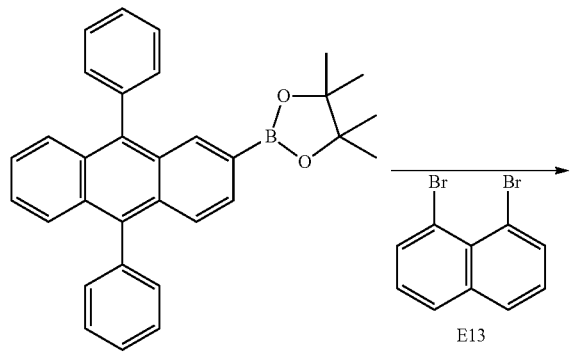

[Chem. 20]

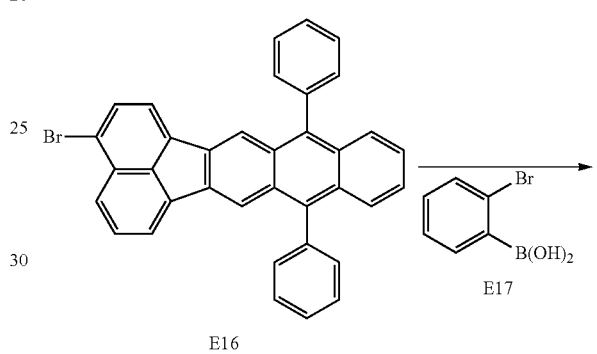

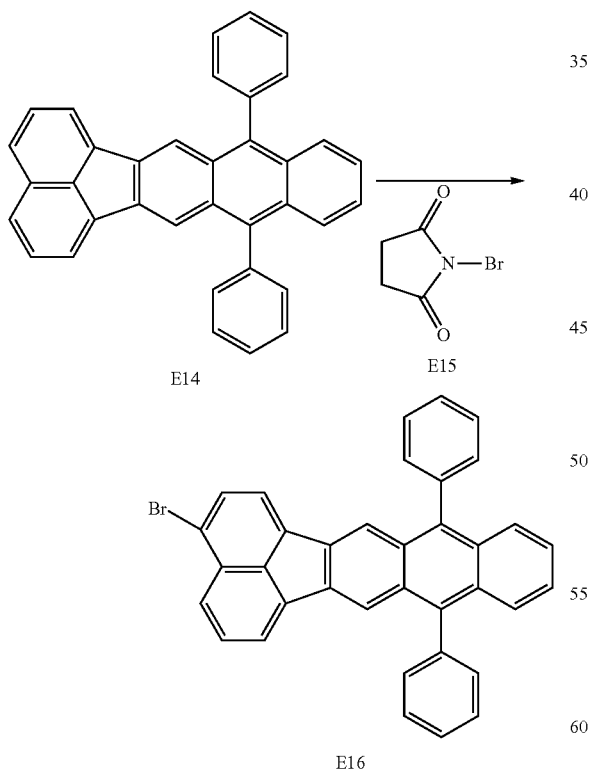

Put in 50 mL of DMF were 2.28 g (5 mmol) of E12 and 2.86 g (10 mmol) of E13. After 0.25 g (0.5 mmol) of bis(triphenylphosphine)palladium(II) dichloride and 2.28 g (15 mmol) of 1,8-diazabicyclo[5.4.0]undec-7-ene were put in the Put in 40 mL of DMF were 2.42 g (5 mmol) of E16 and 1.60 g (8 mmol) of E17. After 0.25 g (0.5 mmol) of bis(triphenylphosphine)palladium(II) dichloride and 2.28 g (15 mmol) of 1,8-diazabicyclo[5.4.0]undec-7-ene were put in the solution, it was heated to 150° C. and was stirred for four hours. After cooling, a precipitate was formed by adding 30 mL of methanol and was filtered out to yield a yellow solid. This solid was purified by column chromatography (chloroform/heptane, 1:3) and was recrystallized twice from chloroform/methanol to yield 1.90 g of a yellow crystal of exemplary compound A3 (yield: 72%).

The purity of this compound was determined to be not less than 99% by HPLC.

The emission spectrum of a toluene solution of exemplary compound A3 with a concentration of $1 \times 10^{-5}$ mol/L was measured by photoluminescence spectroscopy at an excitation wavelength of 350 nm using F-4500 available from Hitachi, Ltd. The resultant spectrum had its maximum intensity at 524 nm.

Example 4

Synthesis of Exemplary Compound A23

The same reaction and purification procedure as in Example 3 was performed except that E8, an organic compound used in Example 3, was changed to E18:

[Chem. 21]

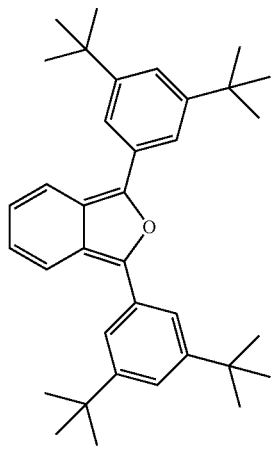

E18

The emission spectrum of a toluene solution of exemplary compound A23 with a concentration of $1\times10^{-5}$ mol/L was measured by photoluminescence spectroscopy at an excitation wavelength of 350 nm using F-4500 available from Hitachi, Ltd. The resultant spectrum had its maximum intensity at 525 nm.

Example 5

Synthesis of Exemplary Compound A13

Exemplary compound A13 was prepared by the same reaction and purification procedure as in Example 1 except that E2, an organic compound used in Example 1, was changed to E19:

[Chem. 22]

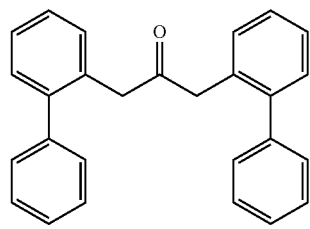

E19

The emission spectrum of a toluene solution of exemplary compound A13 with a concentration of $1\times10^{-5}$ mol/L was measured by photoluminescence spectroscopy at an excitation wavelength of 350 nm using F-4500 available from Hitachi, Ltd. The resultant spectrum had its maximum intensity at 517 nm.

Example 6

Synthesis of Exemplary Compound A21

The same reaction and purification procedure as in Example 1 was performed except that E6, an organic compound used in Example 1, was changed to E20:

[Chem. 23]

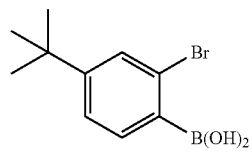

E20

The emission spectrum of a toluene solution of exemplary compound A21 with a concentration of $1\times10^{-5}$ mol/L was measured by photoluminescence spectroscopy at an excitation wavelength of 350 nm using F-4500 available from Hitachi, Ltd. The resultant spectrum had its maximum intensity at 523 nm.

Example 7

Synthesis of Exemplary Compound A25

The same reaction and purification procedure as in Example 1 was performed except that E6, an organic compound used in Example 1, was changed to E20, and E2 was changed to E7.

The emission spectrum of a toluene solution of exemplary compound A25 with a concentration of $1\times10^{-5}$ mol/L was measured by photoluminescence spectroscopy at an excitation wavelength of 350 nm using F-4500 available from Hitachi, Ltd. The resultant spectrum had its maximum intensity at 520 nm.

Example 8

Produced in this example was an organic light-emitting device including an anode, a hole transport layer, a light-emitting layer, a hole/exciton blocking layer, an electron transport layer, and a cathode disposed in the above order. First, a pattern of ITO film having a thickness of 100 nm was formed on a glass substrate. The following organic layers and electrode layers were then continuously formed on the substrate in a vacuum chamber at a pressure of $10^{-5}$ Pa by vacuum deposition using resistance heating so that the electrodes faced each other over an area of 3 mm$^2$.

Hole transport layer (40 nm): G-1

Light-emitting layer (30 nm): host: compound H7 (98% by weight); guest: exemplary compound A2 (2% by weight)

Hole/exciton blocking layer (10 nm): G-3

Electron transport layer (30 nm): G-4

First metal electrode layer (1 nm): LiF

Second metal electrode layer (100 nm): aluminum

[Chem. 24]

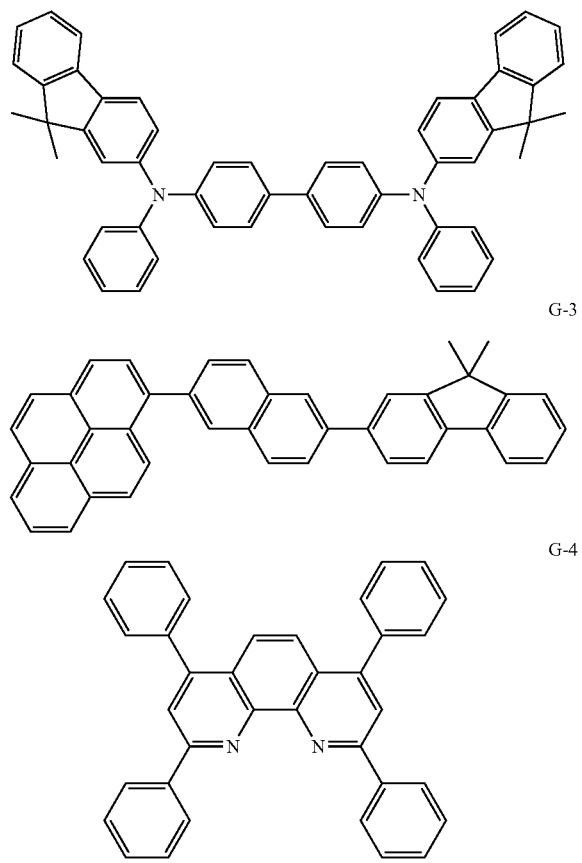

The current-voltage characteristics of the organic light-emitting device were measured using the 4140B pA meter available from Hewlett-Packard Company, and the luminous intensity of the device was measured using BM7 available from Topcon Corporation.

Examples 9 to 20

In Examples 9 to 20, organic light-emitting devices were produced in the same manner as in Example 8 except that the guest and host materials were changed, and were similarly evaluated. The host materials used were the compounds shown in the "G-2" column of Table 5.

Table 5 shows the luminous efficiencies and voltages of Examples 8 to 20.

TABLE 5

| | Guest | G-2 | Luminous efficiency (cd/A) | Voltage (V) |
|---|---|---|---|---|
| Example 8 | A2 | H7 | 16 | 4.5 |
| Example 9 | A2 | H28 | 20 | 4.7 |
| Example 10 | A3 | H13 | 18 | 4.2 |
| Example 11 | A13 | H10 | 20 | 4.9 |
| Example 12 | A22 | H8 | 20 | 4.6 |
| Example 13 | A22 | H17 | 23 | 4.8 |
| Example 14 | A23 | H21 | 20 | 4.6 |
| Example 15 | A23 | H24 | 18 | 4.7 |
| Example 16 | A24 | H6 | 17 | 4.5 |
| Example 17 | A25 | H7 | 22 | 4.6 |
| Example 18 | A25 | H15 | 24 | 4.6 |

TABLE 5-continued

| | Guest | G-2 | Luminous efficiency (cd/A) | Voltage (V) |
|---|---|---|---|---|
| Example 19 | A44 | H3 | 16 | 4.7 |
| Example 20 | A45 | H2 | 20 | 4.6 |

Example 21

Produced in this example was an organic light-emitting device including an anode, a hole injection layer, a hole transport layer, a light-emitting layer, an electron transport layer, an electron injection layer, and a cathode disposed in the above order.

The organic light-emitting device, which had a resonance structure, was produced by the following process.

An aluminum alloy (aluminum-neodymium) was deposited to a thickness of 100 nm on a glass substrate, serving as a support, by sputtering to form a reflective anode. ITO was then deposited to a thickness of 80 nm by sputtering to form a transparent anode. Next, an acrylic device isolation film having a thickness of 1.5 μm was formed around the anode, and an opening having a radius of 3 mm was formed. The substrate was subjected to ultrasonic cleaning with acetone and then with isopropyl alcohol (IPA), followed by washing with boiling IPA and drying. The surface of the substrate was then subjected to ultraviolet/ozone cleaning.

Subsequently, the following organic layers were continuously formed on the substrate in a vacuum chamber at a pressure of $10^{-5}$ Pa by vacuum deposition using resistance heating, and IZO was then deposited to a thickness of 30 nm by sputtering to form a transparent electrode as a cathode. After the cathode was formed, the device was sealed in a nitrogen atmosphere.

In this way, an organic light-emitting device was formed.

Hole injection layer (135 nm): G-11

Hole transport layer (10 nm): G-12

Light-emitting layer (35 nm): host: compound H7 (98% by weight); guest: exemplary compound A13 (2% by weight)

Electron transport layer (10 nm): G-14

Electron injection layer (70 nm): G-15 (80% by weight), lithium (20% by weight)

[Chem. 25]

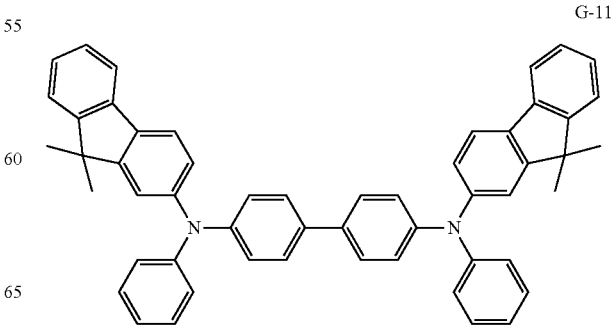

-continued

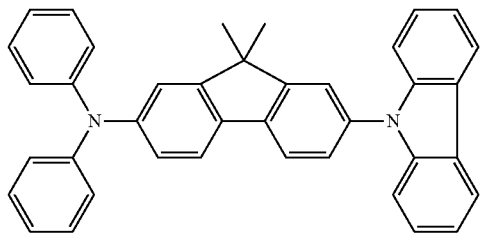

G-12

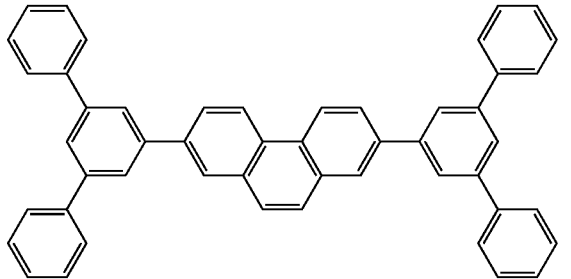

G-14

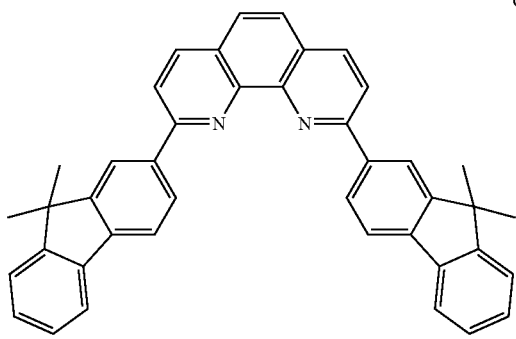

G-15

The current-voltage characteristics of the organic light-emitting device were measured using the 4140B pA meter available from Hewlett-Packard Company, and the luminous intensity of the device was measured using BM7 available from Topcon Corporation.

Examples 22 to 26

In Examples 22 to 26, organic light-emitting devices were produced in the same manner as in Example 21 except that the guest and host materials were changed, and were similarly evaluated. The host materials used were the compounds shown in the "G-13" column of Table 6.

Table 6 shows the luminous efficiencies and voltages of Examples 21 to 26.

TABLE 6

| | Guest | G-13 | Luminous efficiency (cd/A) | Voltage (V) |
|---|---|---|---|---|
| Example 21 | A13 | H7 | 22 | 4.5 |
| Example 22 | A22 | H8 | 25 | 4.3 |
| Example 23 | A23 | H6 | 24 | 4.1 |
| Example 24 | A24 | H10 | 24 | 4.1 |
| Example 25 | A25 | H22 | 26 | 4.0 |
| Example 26 | A44 | H21 | 25 | 4.2 |

Results and Discussion

Organic compounds according to embodiments of the present invention are novel compounds that have high quantum yield and that emit light appropriate as green light and can be used to produce an organic light-emitting device having superior emission characteristics.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-129267, filed Jun. 4, 2010, which is hereby incorporated by reference herein in its entirety.

REFERENCE SIGNS LIST

8 TFT
11 anode
12 organic compound layer
13 cathode

The invention claimed is:

1. An organic compound represented by general formula (1):

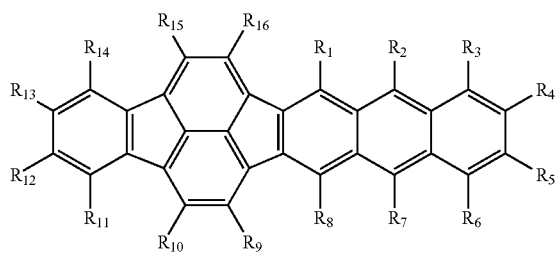

(1)

wherein $R_1$ to $R_{16}$ are each independently selected from the group consisting of a hydrogen atom, a halogen atom, a substituted or unsubstituted alkyl group, a substituted or unsubstituted alkoxy group, a substituted amino group, a substituted or unsubstituted aryl group, and a substituted or unsubstituted heterocyclic group.

2. The organic compound according to claim 1, wherein $R_1$ to $R_{16}$ are each independently selected from the group consisting of a hydrogen atom and a substituted or unsubstituted aryl group.

3. The organic compound according to claim 1, wherein the organic compound is represented by general formula (2):

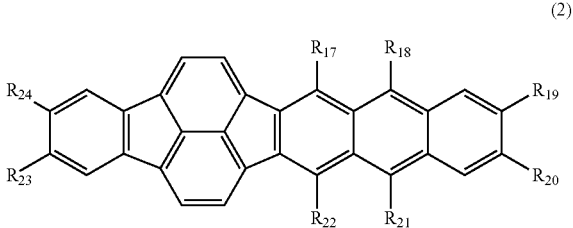

(2)

wherein $R_{17}$ to $R_{24}$ are each independently selected from the group consisting of an alkyl group having one to four carbon atoms and a substituted or unsubstituted aryl group, the aryl group being phenyl, naphthyl, biphenyl, or terphenyl, the aryl group being optionally substituted with an alkyl group having one to four carbon atoms.

4. An organic light-emitting device comprising:
an anode;
a cathode; and
an organic compound layer disposed between the anode and the cathode, the organic compound layer containing the organic compound according to claim 1.

5. An organic light-emitting device comprising:
an anode;
a cathode; and
an organic compound layer disposed between the anode and the cathode, the organic compound layer containing the organic compound according to claim 3.

6. The organic light-emitting device according to claim 4, wherein the organic compound layer is a light-emitting layer.

7. The organic light-emitting device according to claim 6, wherein the organic light-emitting device emits green light.

8. A display apparatus having a plurality of pixels, each including the organic light-emitting device according to claim 4 and a switching device connected to the organic light-emitting device.

9. An image input apparatus comprising:
an image input unit configured to input an image; and
a display unit configured to display the image, the display unit having a plurality of pixels, each including the organic light-emitting device according to claim 4 and a switching device connected to the organic light-emitting device.

10. An illumination apparatus comprising the organic light-emitting device according to claim 4.

11. An exposure light source for electrophotographic image-forming apparatus comprising the organic light-emitting device according to claim 4.

12. An electrophotographic image-forming apparatus comprising an exposure light source, the exposure light source comprising the organic light-emitting device according to claim 4.

* * * * *